(12) United States Patent
Forsell

(10) Patent No.: US 10,195,037 B2
(45) Date of Patent: *Feb. 5, 2019

(54) HIP JOINT METHOD

(71) Applicant: Peter Mats Forsell, Bouveret (CH)

(72) Inventor: Peter Mats Forsell, Bouveret (CH)

( * ) Notice: Subject to any disclaimer, the term of this patent is extended or adjusted under 35 U.S.C. 154(b) by 791 days.

This patent is subject to a terminal disclaimer.

(21) Appl. No.: 14/612,389

(22) Filed: Feb. 3, 2015

(65) Prior Publication Data

US 2015/0150685 A1 Jun. 4, 2015

Related U.S. Application Data

(63) Continuation of application No. 14/600,064, filed on Jan. 20, 2015, which is a continuation of application
(Continued)

(30) Foreign Application Priority Data

Jul. 10, 2009 (SE) ........................................ 0900957
Jul. 10, 2009 (SE) ........................................ 0900958
(Continued)

(51) Int. Cl.
*A61F 2/32* (2006.01)
*A61F 2/36* (2006.01)
(Continued)

(52) U.S. Cl.
CPC .............. *A61F 2/32* (2013.01); *A61B 17/064* (2013.01); *A61B 17/06166* (2013.01);
(Continued)

(58) Field of Classification Search
CPC ...... A61F 2/32; A61F 2/34; A61F 2/36; A61F 2/3609; A61F 2/3621
See application file for complete search history.

(56) References Cited

U.S. PATENT DOCUMENTS 3,918,102 A * 11/1975 Eichler ..................... A61F 2/34
623/22.39
4,731,088 A * 3/1988 Collier ................ A61F 2/30742
623/22.13
(Continued)

FOREIGN PATENT DOCUMENTS

GB 2007980 5/1979
GB 2372707 9/2002

OTHER PUBLICATIONS

International Search Report for PCT/SE2010/050822, dated Oct. 13, 2010.

*Primary Examiner* — Zade Coley
*Assistant Examiner* — Jessica Weiss

(57) ABSTRACT

A method of treating a hip joint of a human patient by providing at least one hip joint surface comprising the steps of: cutting the skin of the human patient, dissecting an area of the pelvic bone on the opposite side from the acetabulum, creating a hole in the dissected area from the opposite side from the acetabulum, the hole passing through the pelvic bone and into the hip joint of the human patient, and providing at least one hip joint surface to the hip joint from the opposite side from the acetabulum, through the hole in the pelvic bone of the human patient.

62 Claims, 27 Drawing Sheets

Related U.S. Application Data

No. 13/383,332, filed as application No. PCT/SE2010/050822 on Jul. 12, 2010, now Pat. No. 8,945,233.

(60) Provisional application No. 61/229,738, filed on Jul. 30, 2009, provisional application No. 61/229,739, filed on Jul. 30, 2009, provisional application No. 61/229,743, filed on Jul. 30, 2009, provisional application No. 61/229,745, filed on Jul. 30, 2009, provisional application No. 61/229,746, filed on Jul. 30, 2009, provisional application No. 61/229,747, filed on Jul. 30, 2009, provisional application No. 61/229,748, filed on Jul. 30, 2009, provisional application No. 61/229,751, filed on Jul. 30, 2009, provisional application No. 61/229,752, filed on Jul. 30, 2009, provisional application No. 61/229,755, filed on Jul. 30, 2009, provisional application No. 61/229,761, filed on Jul. 30, 2009, provisional application No. 61/229,767, filed on Jul. 30, 2009, provisional application No. 61/229,778, filed on Jul. 30, 2009, provisional application No. 61/229,786, filed on Jul. 30, 2009, provisional application No. 61/229,789, filed on Jul. 30, 2009, provisional application No. 61/229,796, filed on Jul. 30, 2009, provisional application No. 61/229,735, filed on Jul. 30, 2009.

(30) Foreign Application Priority Data

| Jul. 10, 2009 | (SE) | 0900959 |
|---|---|---|
| Jul. 10, 2009 | (SE) | 0900960 |
| Jul. 10, 2009 | (SE) | 0900962 |
| Jul. 10, 2009 | (SE) | 0900963 |
| Jul. 10, 2009 | (SE) | 0900965 |
| Jul. 10, 2009 | (SE) | 0900966 |
| Jul. 10, 2009 | (SE) | 0900968 |
| Jul. 10, 2009 | (SE) | 0900969 |
| Jul. 10, 2009 | (SE) | 0900970 |
| Jul. 10, 2009 | (SE) | 0900972 |
| Jul. 10, 2009 | (SE) | 0900973 |
| Jul. 10, 2009 | (SE) | 0900974 |
| Jul. 10, 2009 | (SE) | 0900976 |
| Jul. 10, 2009 | (SE) | 0900978 |
| Jul. 10, 2009 | (SE) | 0900981 |

(51) Int. Cl.

| A61F 2/34 | (2006.01) |
|---|---|
| A61B 17/16 | (2006.01) |
| A61B 17/06 | (2006.01) |
| A61B 17/064 | (2006.01) |
| A61B 17/34 | (2006.01) |
| A61F 2/28 | (2006.01) |
| A61L 24/00 | (2006.01) |
| A61B 90/00 | (2016.01) |
| A61F 2/30 | (2006.01) |
| A61B 17/74 | (2006.01) |
| A61B 17/86 | (2006.01) |
| A61F 2/46 | (2006.01) |

(52) U.S. Cl.
CPC ...... *A61B 17/1637* (2013.01); *A61B 17/1659* (2013.01); *A61B 17/1664* (2013.01); *A61B 17/1666* (2013.01); *A61B 17/3468* (2013.01); *A61B 17/3472* (2013.01); *A61B 90/361* (2016.02); *A61F 2/28* (2013.01); *A61F 2/30756* (2013.01); *A61F 2/34* (2013.01); *A61F 2/3601* (2013.01); *A61F 2/3603* (2013.01); *A61F 2/3609* (2013.01); *A61F 2/4603* (2013.01); *A61F 2/4607* (2013.01); *A61F 2/4609* (2013.01); *A61L 24/00* (2013.01); *A61B 17/1668* (2013.01); *A61B 17/74* (2013.01); *A61B 17/86* (2013.01); *A61F 2002/305* (2013.01); *A61F 2002/30331* (2013.01); *A61F 2002/30378* (2013.01); *A61F 2002/30433* (2013.01); *A61F 2002/30448* (2013.01); *A61F 2002/30449* (2013.01); *A61F 2002/30451* (2013.01); *A61F 2002/30462* (2013.01); *A61F 2002/30464* (2013.01); *A61F 2002/30469* (2013.01); *A61F 2002/30471* (2013.01); *A61F 2002/30472* (2013.01); *A61F 2002/30476* (2013.01); *A61F 2002/30497* (2013.01); *A61F 2002/30507* (2013.01); *A61F 2002/30558* (2013.01); *A61F 2002/30563* (2013.01); *A61F 2002/30565* (2013.01); *A61F 2002/30579* (2013.01); *A61F 2002/30594* (2013.01); *A61F 2002/30616* (2013.01); *A61F 2002/30818* (2013.01); *A61F 2002/30878* (2013.01); *A61F 2002/30886* (2013.01); *A61F 2002/3241* (2013.01); *A61F 2002/3483* (2013.01); *A61F 2002/3611* (2013.01); *A61F 2002/3615* (2013.01); *A61F 2002/3619* (2013.01); *A61F 2002/3631* (2013.01); *A61F 2002/4631* (2013.01); *A61F 2002/4635* (2013.01); *A61F 2002/4677* (2013.01); *A61F 2220/0025* (2013.01)

(56) References Cited

U.S. PATENT DOCUMENTS

| 5,320,625 | A | * | 6/1994 | Bertin | A61B 5/22 606/91 |
|---|---|---|---|---|---|
| 6,010,535 | A | * | 1/2000 | Shah | A61F 2/32 623/22.16 |
| 2003/0050704 | A1 | * | 3/2003 | Keynan | A61B 17/72 623/22.12 |
| 2003/0060890 | A1 | * | 3/2003 | Tarabishy | A61B 17/1617 623/22.12 |
| 2006/0229624 | A1 | * | 10/2006 | May | A61B 17/32002 606/79 |
| 2006/0235539 | A1 | * | 10/2006 | Blunn | A61B 17/1666 623/22.12 |
| 2007/0173946 | A1 | * | 7/2007 | Bonutti | A61B 17/025 623/20.14 |
| 2009/0005871 | A1 | * | 1/2009 | White | A61B 17/562 623/17.11 |

\* cited by examiner

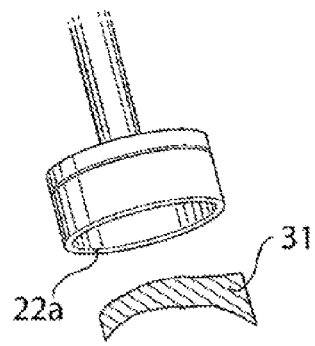
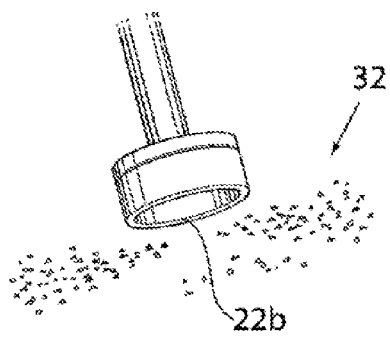
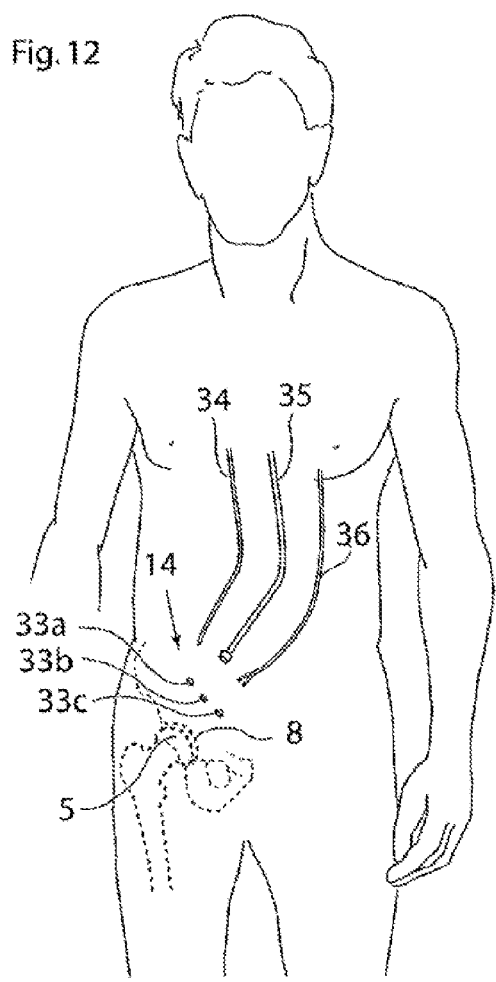

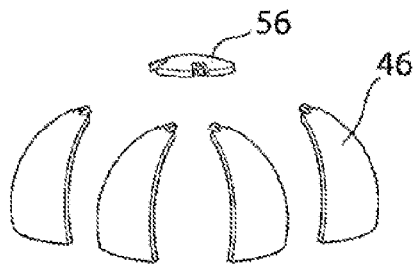
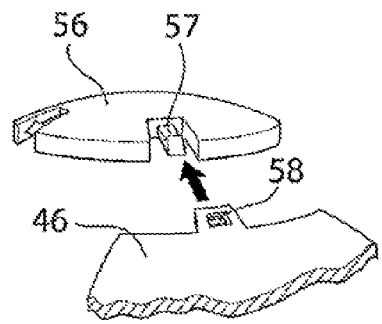
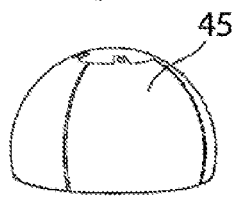
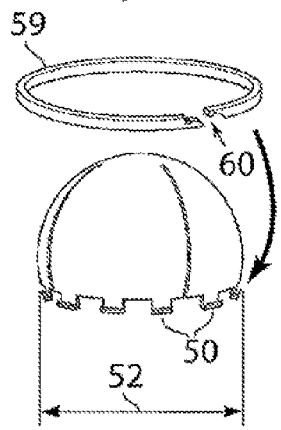
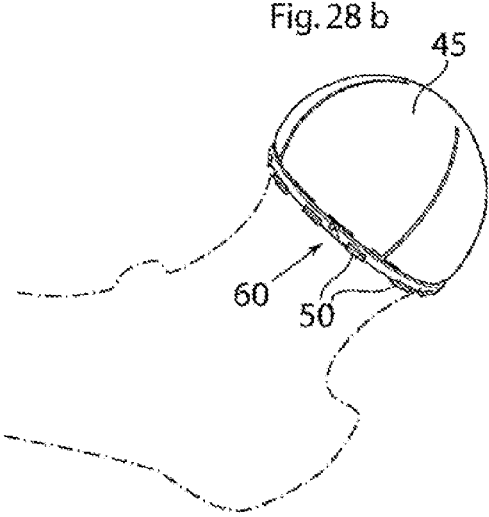
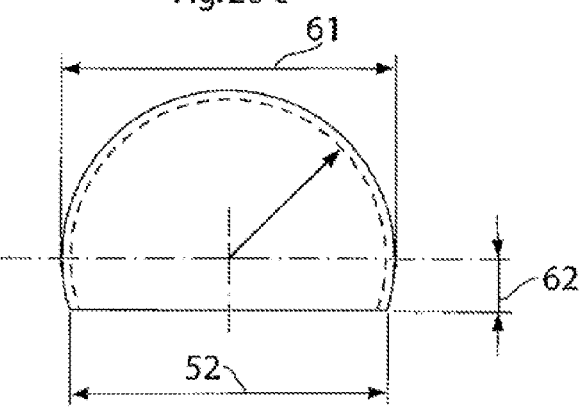

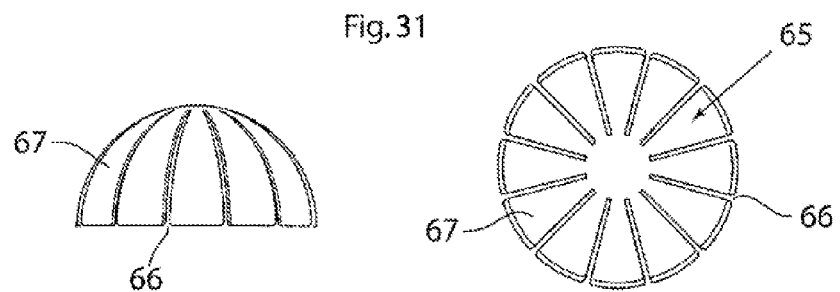
Fig. 31
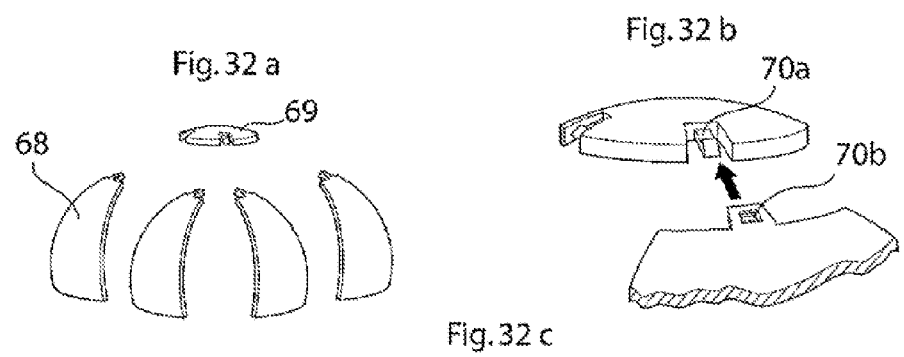
Fig. 32 a   Fig. 32 b
Fig. 32 c
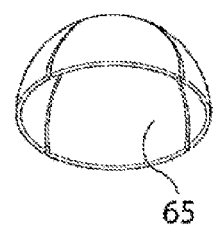
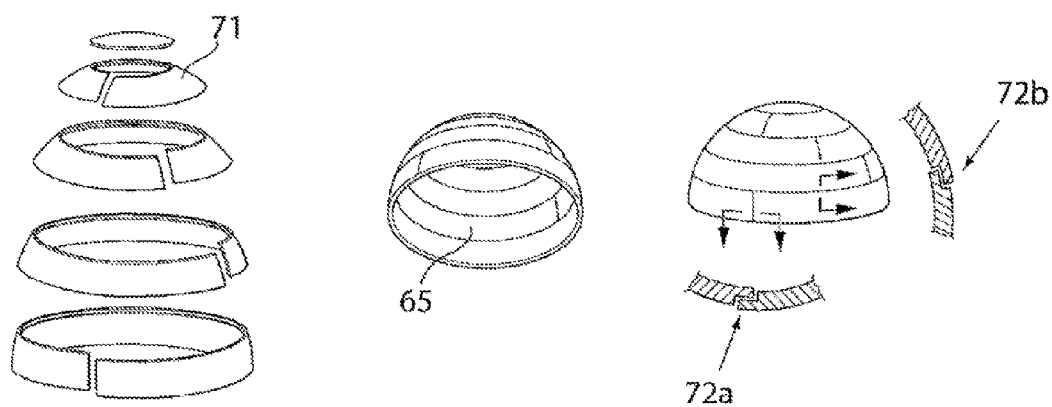
Fig. 33 a   Fig. 33 b   Fig. 33 c

65

73b

73a

73a

73b 73a  74  73a

75

67
66
65
66
67
67

67
66

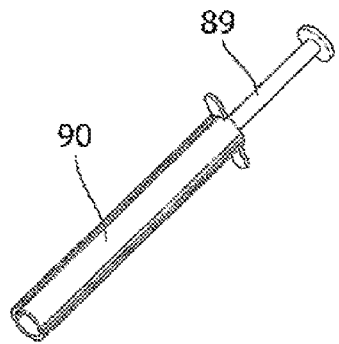
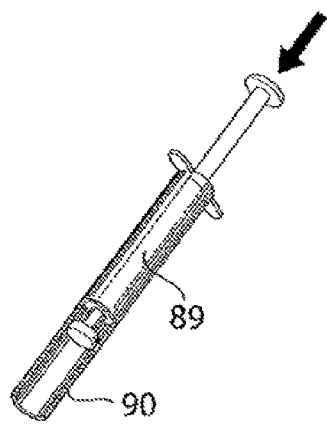
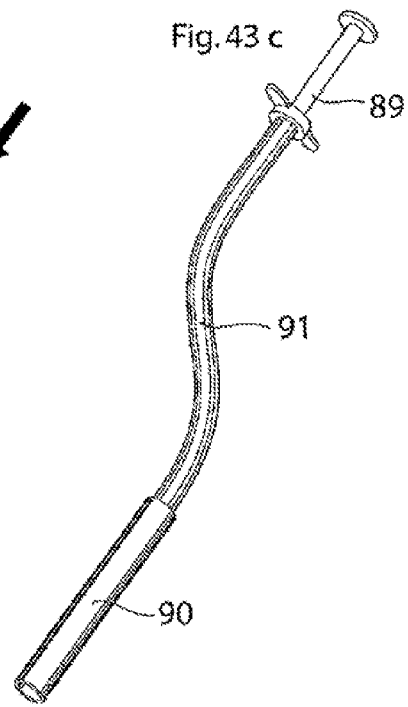
Fig. 43 a  Fig. 43 b  Fig. 43 c
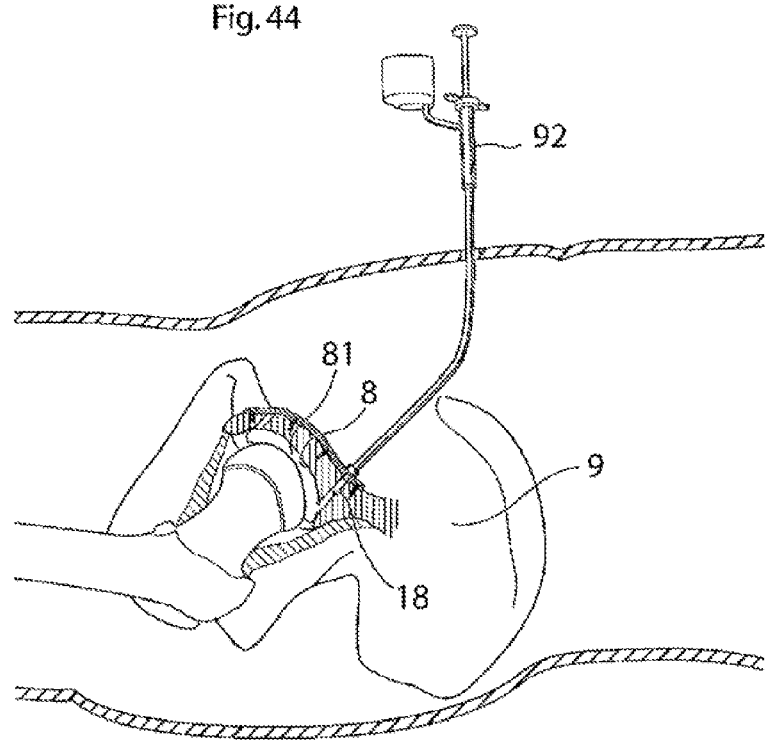
Fig. 44

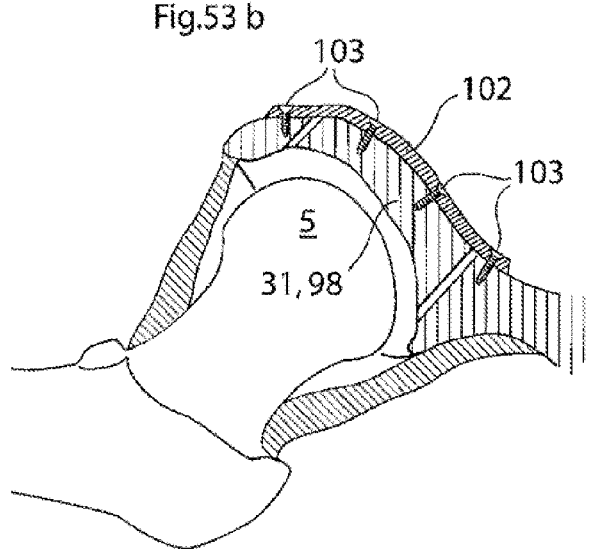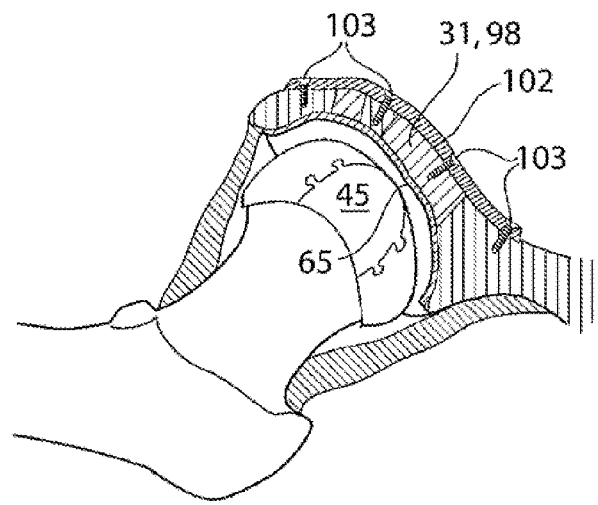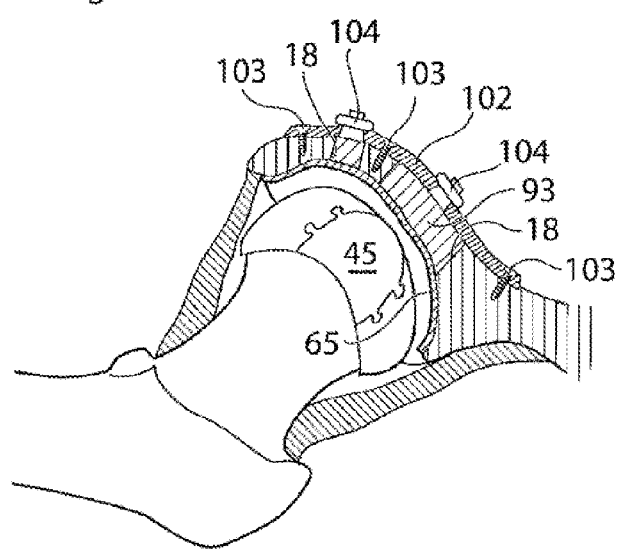

HIP JOINT METHOD

This application is a continuation of U.S. patent application Ser. No. 14/611,296 filed Jan. 20, 2015, which is a continuation of U.S. patent application Ser. No. 13/383,332 filed Jan. 10, 2012, issued as U.S. Pat. No. 8,945,233 on Feb. 3, 2015, which is the U.S. national phase of International Application No. PCT/SE2010/050822, filed Jul. 12, 2010, which designates the US and claims priority to Swedish Application Nos. 0900981-2; 0900957-2, 0900959-8, 0900960-6, 0900962-2; 0900963-0; 0900965-5; 0900966-3; 0900968-9; 0900969-7; 0900970-5; 0900972-1; 0900973-9; 0900974-7; 0900976-2; 0900978-8 and 0900958-0, all filed Jul. 10, 2009, and which claims the benefit of U.S. Provisional Nos. 61/229,738; 61/229,739; 61/229,743; 61/229,745; 61/229,746; 61/229,747; 61/229,748; 61/229,751; 61/229,752; 61/229,755; 61/229,761; 61/229,767; 61/229,778; 61/229,786; 61/229,789; 61/229,796 and 61/229,735 all filed on Jul. 30, 2009, respectively, the entire contents of each of which are hereby incorporated by reference.

FIELD OF INVENTION

The present invention relates generally to a surgical or laparoscopic/arthroscopic method of operating a hip joint of a human patient.

BACKGROUND

Hip joint Osteoarthritis is a syndrome in which low-grade inflammation results in pain in the hip joints, caused by abnormal wearing of the cartilage that acts as a cushion inside if the hip joint. This abnormal wearing of the cartilage also results in a decrease of the joints lubricating fluid called Synovial fluid. Hip joint Osteoarthritis is estimated to affect 80% of all people over 65 years of age, in more or less serious forms.

The present treatment for hip osteoarthritis comprises NSAID drugs, local injections of Hyaluronic acid or Glucocorticoid to help lubricate the hip joint, and replacing parts of the hip joint with a prosthesis through hip joint surgery.

The replacing of parts of the hip joint is one of the most common surgeries to date performed at hundreds of thousands of patients in the world every year. The most common method comprises placing a metal prosthesis in femur and a plastic bowl in acetabulum. This operation is done through a lateral incision in the hip and upper thigh and through fascia lata and the lateral muscles of the thigh. To get access to the joint, the supporting hip joint capsule attached to femur and ilium of pelvis needs to be penetrated, making it difficult to get a fully functional joint after the surgery. Femur is then cut at the neck with a bone saw and the prosthesis is placed in femur either with bone cement or without. Acetabulum is slightly enlarged using an acetabular reamer, and the plastic bowl is positioned using screws or bone cement.

The surgery typically requires one week of hospitalization due to the increased risk of infection. The recovery process is on average about 6 weeks, but even after this period the patient should not perform any physical activates that places large strain on the joint.

It would therefor be desirable to have an operational method that could spare the hip joint capsule and reduce the removal of healthy femur bone. It would further be preferable to have a method of operating that could shorten the time for recovery of the patient, and reducing the amount of affected large blood vessels, thus reducing the risk of blood clots.

SUMMARY

The Surgical and Laparoscopic/Arthroscopic Method

A first object is to provide a surgical and/or laparoscopic/arthroscopic method for treating a hip joint of a human patient by providing at least one hip joint surface. The hip joint comprises a caput femur located on the very top of the femur bone and an acetabulum, which is a part of the pelvic bone, the caput femur is in connection with the acetabulum.

The idea is to perform an operation in the hip joint through a hole in the pelvic bone, however some of the aspects of the present invention can be performed using conventional surgery entering the hip joint through the hip joint capsule, or by entering through the femur bone.

The surgical method comprises the steps of cutting the skin of the human patient, dissecting an area of the pelvic bone on the opposite side from acetabulum, creating a hole in the dissected area which passes through the pelvic bone and into the hip joint, and providing at least one hip joint surface into the hip joint, through the hole in the pelvic bone.

According to one embodiment, the step of cutting the skin of the human patient could be performed in the abdominal wall, the inguinal area, the pelvic region or the abdominal region of the patient.

The laparoscopic/arthroscopic method comprises the steps of inserting a needle or a tube like instrument into the abdominal region, pelvic region or inguinal region of the patient's body, using the needle or tube like instrument to fill the patient's body with gas, placing at least two laparoscopic/arthroscopic trocars in the patient's body, and inserting a camera through one of the laparoscopic/arthroscopic trocars into the patient's body. At least one dissecting tool is inserted through one of said at least two laparoscopic/arthroscopic trocars, after which an area of the pelvic bone on the opposite side from said acetabulum is dissected. Furthermore the method comprises the steps of creating a hole in said dissected area that passes through the pelvic bone and into the hip joint of the human patient, and providing at least one hip joint surface to the hip joint, through the hole in the pelvic bone.

According to one embodiment, the step of inserting a needle or tube like instrument is performed in the abdominal wall, the inguinal area, the pelvic region or the abdominal region of the patient.

The step of dissecting an area of the pelvic bone performed in both the surgical and the laparoscopic/arthroscopic method could be performed in the abdominal cavity, an area between peritoneum and the pelvic bone, an area of the pelvic bone and surrounding tissue, the pelvic area or an area of the pelvic bone that comprises the inguinal area. Dissecting a combination of the above mentioned areas is also conceivable. It is obvious that the methods described may both be combined or altered reaching the same goal to dissect the pelvic bone on the opposite side of the acetabulum.

The surgical or laparoscopic/arthroscopic method could further comprise the step of reaming the caput femur and/or the acetabulum, e.g. by means of an expandable reamer.

According to one embodiment the artificial hip joint surface could be fixated to the pelvic bone or to the caput femur after the step of providing said hip joint surface. The fixation could be performed by means of mechanical fixating members, such as screws or plates, adhesive, bone cement, or a combination thereof. When the artificial hip joint surface has been placed in the hip joint, the surgical or laparoscopic/arthroscopic method could further comprise the step of closing the hole in the pelvic bone using a bone plug, a prosthetic part, bone cement, or a combination thereof.

According to another embodiment the artificial hip joint surface is provided by means of a mould placed in the hip joint through a hole in the pelvic bone, the hip joint capsule or the femur bone. Said artificial hip joint surface could comprise an artificial acetabulum surface and/or an artificial caput femur surface. After the mould has been inserted into the hip joint a fluid is injected which serves as an artificial caput femur surface after hardening. It is conceivable that said mould is resorbable by the human body or made of a material adapted to melt.

According to yet another embodiment the artificial hip joint surface is provided by injecting a fluid into a sealed area of the hip joint. Said artificial hip joint surface could comprise an artificial acetabulum surface and/or an artificial caput femur surface. The sealed area is sealed by means of at least one sealing member placed in said hip joint through a hole in the pelvic bone, the hip joint capsule or the femur bone. It is conceivable that said at least one sealing member is resorbable by the human body or made of a material adapted to melt.

After the steps of the surgical method have been performed, the instruments are withdrawn and the skin is closed using sutures or staples.

The Acetabulum Surface

According to one embodiment, the step of providing an artificial acetabulum surface comprises providing an artificial acetabulum surface adapted to be inserted into the hip joint through a hole in the pelvic bone and to be in connection with the pelvic bone and carry the load placed on the caput femur from the weight of the patient by the connection with the pelvic bone. It is conceivable that the diameter of the hole is larger than the largest diameter of the artificial acetabulum surface thus allowing the artificial acetabulum surface to pass through the hole in its entirety, however it is also conceivable that said hole is smaller than the largest diameter of the artificial acetabulum surface thus hindering the artificial acetabulum surface from passing through the hole, which makes it possible for the edges of said hole to carry the load placed on said acetabulum from the weight of the patient.

According to one embodiment, the step of providing an artificial acetabulum surface comprises providing an artificial acetabulum surface comprising at least one supporting member which in turn could comprise at least one screw, adhesive, at least one plate, bone cement, a section of the artificial acetabulum surface or a combination of the mentioned alternatives. It is also conceivable that the supporting member comprises a first and second part. The second part is displaceable in relation to the first part and adapted to carry a load by the connection with the pelvic bone, and carries the load when displaced.

According to one embodiment, the step of providing an artificial acetabulum surface comprises providing an artificial acetabulum surface comprising at least two acetabulum surface parts. The at least two artificial acetabulum surface parts are adapted to be connected to each other after insertion in a hip joint of a human patient to form an artificial acetabulum surface. The two artificial caput femur surface parts could be adapted to be mechanically connected using at least one of: at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members.

The artificial acetabulum being severable enables the insertion of the artificial acetabulum surface through a hole smaller than the artificial acetabulum surface which makes it possible for the edges of said hole to carry the load placed on said acetabulum from the weight of the human patient.

According to one embodiment, the step of providing an artificial acetabulum surface comprises providing an artificial acetabulum surface adapted to have a varying largest diameter for insertion through a hole in the pelvic bone from the opposite side from acetabulum, and the diameter of said artificial acetabulum surface varies when said artificial acetabulum surface is being inserted through said hole in the pelvic bone. Since the largest diameter of the artificial acetabulum surface is adapted to vary between being both smaller and larger than the hole in the pelvic bone, the hole could having a diameter smaller than the largest diameter of the artificial acetabulum surface.

The surgical or laparoscopic/arthroscopic method could comprise the step of inserting the artificial acetabulum surface adapted to have a varying largest diameter through the hole in the pelvic bone. In this embodiment it is conceivable that the artificial acetabulum surface is adapted to be flexible in its construction, thus enabling the insertion of said artificial acetabulum surface through a hole in the pelvic bone that is smaller than said largest diameter of the artificial acetabulum surface. The flexible part of the artificial acetabulum surface could further be adapted to expand after insertion through the hole making the largest diameter of the artificial acetabulum surface larger than the diameter of the hole in the pelvic bone, thus hindering the artificial acetabulum surface from passing through the hole.

Caput Femur Surface

According to one embodiment, the step of providing at least one hip joint surface comprises the step of providing an artificial caput femur surface adapted to be in connection with said acetabulum surface. It is conceivable that the diameter of the hole is larger than the largest diameter of the caput femur thus allowing the caput femur to pass through the hole. However it is also conceivable that said hole is smaller than the largest diameter of the caput femur thus hindering the caput femur from passing through the hole.

According to one embodiment, the step of providing an artificial caput femur surface comprises providing an artificial caput femur surface comprising at least two caput femur surface parts adapted to be connected to each other after insertion in a hip joint to form an artificial caput femur surface. According to one embodiment the at least two artificial caput femur surface parts are inserted through a hole in the pelvic bone from the opposite side from acetabulum, said hole having a diameter less than the largest diameter of said artificial caput femur surface. The mechanical connection that connects the parts of the artificial caput femur surface could be created using screws, form fitting, welding, sprints, band, adhesive or some other mechanical connecting member.

According to one embodiment the step of providing an artificial caput femur surface comprises providing an artificial caput femur surface adapted to have a varying largest diameter and having a largest diameter that varies for insertion through a hole in the pelvic bone from the opposite side from acetabulum of said human patient. Since the largest diameter of the artificial caput femur surface varies between being both smaller and larger than the hole in the pelvic bone, the hole could have a diameter smaller than the largest diameter of the artificial caput femur surface.

According to one embodiment, the step of providing an artificial caput femur surface comprises the step of inserting the artificial caput femur surface adapted to have a varying largest diameter through the hole in the pelvic bone. In this embodiment it is conceivable that the artificial caput femur surface is adapted to be flexible in its construction, and is flexible in its construction when being inserted through a hole in the pelvic bone that is smaller than said largest diameter of the artificial caput femur surface. The flexible part of the artificial caput femur surface could further be adapted to expand, and expands, after insertion through the hole making the largest diameter of the artificial caput femur surface larger than the diameter of the hole in the pelvic bone, thus hindering the artificial caput femur surface from passing through the hole.

According to one embodiment, the step of providing an artificial caput femur surface comprises the step of providing at least two artificial caput femur surface parts. These at least two artificial caput femur surface parts are adapted to be connected, and connects to each other to form an artificial caput femur surface having a greatest internal cross-sectional area. The artificial caput femur surface is hollow and has an opening with a cross-sectional area smaller than the greatest internal cross-sectional area of the artificial caput femur, i.e. said artificial caput femur surface is larger than equator frustum spherical.

According to one embodiment, the step of providing an artificial caput femur surface comprises the step of providing an artificial caput femur surface that is hollow and has a greatest internal cross-sectional area and an opening with an area less than said greatest internal cross-sectional area of said artificial caput femur surface when mounted on the caput femur. The artificial caput femur surface further comprises at least one slit allowing said artificial caput femur surface to be mounted on said caput femur, which requires a diameter larger that the diameter of caput femur, and an opening smaller than said greatest internal cross-sectional area.

The surgical or laparoscopic/arthroscopic method could further comprise the steps of, inserting at least two artificial caput femur surface parts into the hip joint and mounting the at least two artificial caput femur surface parts on the hip joint to form an artificial caput femur surface. The artificial caput femur surface could be mechanically fixated to the caput femur by means of the mounting on the caput femur, i.e. the artificial caput femur surface can not be removed without dismounting the artificial caput femur surface parts.
Instruments According to one embodiment the above mentioned step of reaming the acetabulum and/or the caput femur is performed by means of an expandable reamer after the step of inserting said expandable reamer through a hole in the pelvic bone has been performed.

The expandable reamer could be adapted to be inserted through a hole in the pelvic bone and could be adapted to be bent using one or more fixed angles, adjustable angles or parallel displaced parts or sections.

According to one embodiment the hole in said dissected area could be created using a surgical instrument creating a through-going hole in the acetabulum area from the abdominal side of the pelvic bone of said human patient through repetitive or continuous movement.

The surgical instrument could be adapted to create a through-going hole in the acetabulum area from the abdominal side of the pelvic bone of said human patient through repetitive or continuous movement. Furthermore the surgical instrument could comprise a driving member, a bone contacting organ in connection with said driving member and an operating device adapted to operate said driving member.

According to one embodiment the step of creating a through-going hole in the acetabulum area from the abdominal side of the pelvic bone is performed using a surgical instrument adapted to create a through-going hole in the pelvic bone further adapted to be bent using one or more fixed angles, adjustable angles or parallel displaced parts or sections. It is furthermore conceivable that said instrument could be adapted to ream the acetabulum and/or the caput femur, e.g. by means of the bone contacting organ being replaceable.

According to one embodiment the surgical or laparoscopic/arthroscopic method comprises the step of dissecting in the dissecting area. In this embodiment it is further conceivable that said dissecting is performed using a dissecting tool adapted to dissect an area of the pelvic bone from the opposite side from acctabulum.

According to one embodiment the surgical or laparoscopic/arthroscopic method comprises the step of placing a mould in the hip joint. In this embodiment it is further conceivable that said mould is placed in the hip joint through at least one of, the hip joint capsule, the pelvic bone, or the femur bone using a mould placing instrument. This instrument could be adapted to place a mould in the hip joint of a human patient, furthermore said instrument could be equipped with a fixed angle, an adjustable angle or a parallel displaced part or section for improved reach.

According to another embodiment the above mentioned surgical or laparoscopic/arthroscopic method comprises the step of placing at least one sealing member in the hip joint. In this embodiment it is further conceivable that the sealing member is placed in the hip joint through at least one of, the hip joint capsule, the pelvic bone, or the femur bone using an instrument adapted therefor. This instrument could be equipped with a fixed angle, an adjustable angle or a parallel displaced part or section for improved reach.

According to some of the above mentioned embodiments, the step of providing an artificial caput femur or acetabulum surface comprises the steps of providing at least two artificial acetabulum/caput femur surface parts. According to these embodiments the surgical or laparoscopic/arthroscopic method could comprise the step of inserting these at least two artificial acetabulum/caput femur surface parts, in which case a surgical instrument adapted therefor could be used. Said instrument could be adapted to insert the parts through at least one of, the hip joint capsule, the pelvic bone, or the femur bone. It is furthermore conceivable that said instrument is equipped with a fixed angle, an adjustable angle or a parallel displaced part or section for improved reach.

According to one embodiment the driving member and bone contacting organ together from an elongated member, placing said elongated member achieving a first supporting point for the bone contacting organ in the femoral bone and a second supporting point in a pelvic bone.

According to one embodiment, an operating device giving force to said driving member from outside the body, lateral on the opposite side of said hip joint outside the opposite side ilium pelvic bone outside the body. The elongated member could be adapted to receiving force from an operation device in the abdomen.

According to another embodiment, the elongated member is adapted to receive said force from an operation device outside the body, lateral of the proximal femoral bone.

BRIEF DESCRIPTION OF DRAWINGS

The invention is now described, by way of example, with reference to the accompanying drawings, in which:

FIG. 10 shows the bone contacting organ according to a first embodiment, FIG. 11 shows the bone contacting organ according to a second embodiment, FIG. 12 shows the laparoscopic/arthroscopic method of operating the hip joint of a human patient, FIG. 27a shows the artificial caput femur surface according to a fifth embodiment, FIG. 27b shows the artificial caput femur surface according to the fifth embodiment in greater detail, FIG. 27c shows the artificial caput femur surface according to the fifth embodiment when assembled, FIG. 28a shows the artificial caput femur surface according to a sixth embodiment, FIG. 28b shows the artificial caput femur surface according to a sixth embodiment when fixated to the caput femur, FIG. 28c shows an artificial caput femur surface being larger than equator frustum spherical, FIG. 31 shows an artificial acetabulum surface according to a first embodiment, FIG. 32a shows an artificial acetabulum surface according to a second embodiment, FIG. 32b shows an artificial acetabulum surface according to the second embodiment in greater detail, FIG. 32c shows the artificial acetabulum surface when assembled, FIG. 33a shows an artificial acetabulum surface according to a third embodiment, FIG. 33b shows an artificial acetabulum surface according to the third embodiment when assembled, FIG. 33c shows the connection function of the artificial acetabulum surface according to the third embodiment.

FIG. 43a shows an instrument for insertion of a mould or a sealing member into a hip joint, FIG. 43b shows the instrument for insertion of a mould or a sealing member into a hip joint in section, FIG. 43c shows the instrument for insertion of a mould or a sealing member into a hip joint according to a second embodiment, FIG. 44 shows the insertion of fluid into an area of the hip joint.

DEFINITIONS

Figure 1:
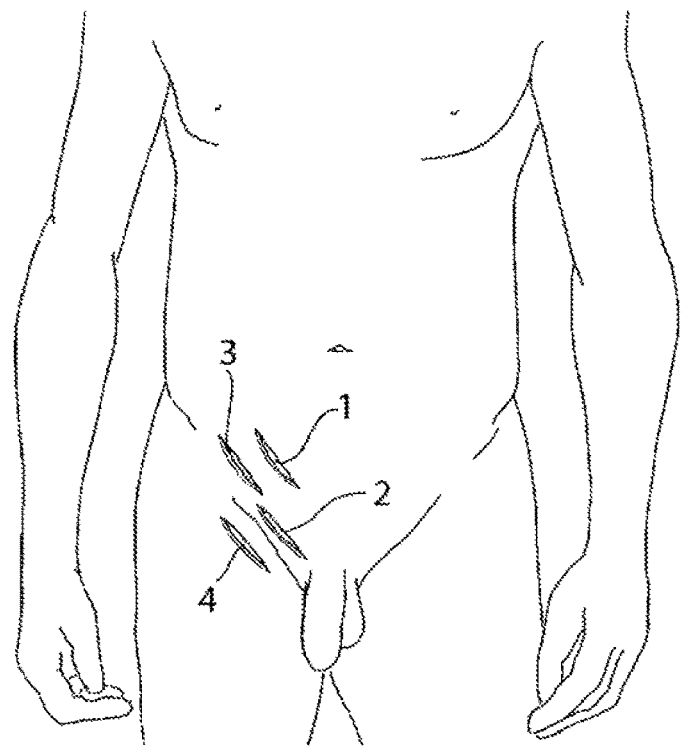
FIG. 1 shows different locations of the incisions made in the human body in the surgical method.

Functional position size and full functional size is the size of the artificial hip joint surface when it performs its function of working as a hip joint surface inside of the hip joint.

Frustum spherical is a geometric shape wherein a section of a sphere has been removed from a full sphere along a cross-sectional area of the sphere. Larger than equator frustum spherical aims to illustrate that the section removed from the sphere is smaller than the remainder so that the surface of the sphere still covers more than half of a full sphere and thus passes beyond the equator of said full sphere. An illustration of the larger than equator frustum spherical artificial caput femur surface is given in FIG. 28c.

The largest diameter of caput femur is the largest diameter of the sphere shaped caput femur that could be created with a radius substantially perpendicular to the collum femur bone.

A cross-sectional distance is the distance between two or more elements located on a common three dimensional geometrical structure. According to one embodiment a cross sectional distance is the distance between two elements on an artificial caput femur surface, wherein said two elements produces a spherical shape having said cross-section.

Functional hip movements are to be understood as movements of the hip that at least partly correspond to the natural movements of the hip. On some occasions the natural movements of the hip joint might be somewhat limited or altered after hip joint surgery, which makes the functional hip movements of a hip joint with artificial surfaces somewhat different than the functional hip movements of a natural hip joint.

The functional position of an implantable medical device or prosthesis is the position in which the hip joint can perform functional hip movements. The final position is to be understood as a functional position in which the medical device needs no further position change.

Biocompatible material is to be understood as being a material with low level of immune response. Biocompatible materials are sometimes also referred to as biomaterials. Analogous is biocompatible metals a biocompatible metal with low immune response such as titanium or tantalum. The biocompatible metal could also be a biocompatible alloy comprising at least one biocompatible metal.

Form fitting is to be understood as an element having a part or section which is adapted to enable a mechanical connection of said element to at least one other element using said part or section. Form fitted structure is a structure of an element which enables form fitting.

DETAILED DESCRIPTION

In the following a detailed description of embodiments of the present invention will be given. In the drawing figures, like reference numerals designate identical or corresponding elements throughout the several figures. It will be appreciated that these figures are for illustration only and are not in any way restricting the scope of the invention. Thus, any references to direction, such as "up" or "down", are only referring to the directions shown in the figures. Also, any dimensions etc. shown in the figures are for illustration purposes.

The medical device according to any of the embodiments could comprise at least one material selected from a group consisting of: polytetrafluoroethylene (PTFE), perfluoroalkoxy (PFA) and fluorinated ethylene propylene (FEP). It is furthermore conceivable that the material comprises a metal alloy, such as cobalt-chromium-molybdenum or titanium or stainless steel, or polyethylene, such as cross-linked polyethylene or gas sterilized polyethylene. The use of ceramic material is also conceivable, in the contacting surfaces or the entire medical device such as zirconium or zirconium dioxide ceramics or alumina ceramics. The part of the medical device in contact with human bone for fixation of the medical device to human bone could comprise a poorhouse structure which could be a porous micro or nano-structure adapted to promote the growth-in of human bone in the medical device for fixating the medical device. The porous structure could be achieved by applying a hydroxy-apatite (HA) coating, or a rough open-pored titanium coating, which could be produced by air plasma spraying, a combination comprising a rough open-pored titanium coating and a HA top layer is also conceivable. The contacting parts could be made of a self lubricated material such as a waxy polymer, such as PTFE, PFA, FEP, PE and UHMWPE, or a powder metallurgy material which could be infused with a lubricant, which preferably is a biocompatible lubricant such as a Hyaluronic acid derivate. It is also conceivable that the material of contacting parts or surfaces of the medical device herein is adapted to be constantly or intermittently lubricated. According to some embodiments the parts or portions of the medical device could comprise a combination of metal materials and/or carbon fibers and/or boron, a combination of metal and plastic materials, a combination of metal and carbon based material, a combination of carbon and plastic based material, a combination of flexible and stiff materials, a combination of elastic and less elastic materials, Corian or acrylic polymers.

FIG. 1 shows a frontal view of the body of a human patient. A surgical method of operating the hip joint from the opposite side from acetabulum, is according to a first embodiment performed starting with an incision 1 in the abdominal wall of the human patient. The incision 1 passes through the rectus abdominis and peritoneum in to the abdomen of the human patient. In a second preferred embodiment the incision 2 is conducted through the abdominal wall, preferably rectus abdominis and in to the pelvic area, below peritoneum. According to a third embodiment the incision 3 is performed just between Illium and the surrounding tissue, an incision 3 which could enable the pelvic bone to be dissected with very little penetration of fascia and muscular tissue. According to a fourth embodiment the incision 4 is made in the inguinal channel. In all of the four embodiments the tissue surrounding the pelvic bone 9 in the area opposite to acetabulum is removed or penetrated which enables the surgeon to reach the pelvic bone 9.

Figure 2:
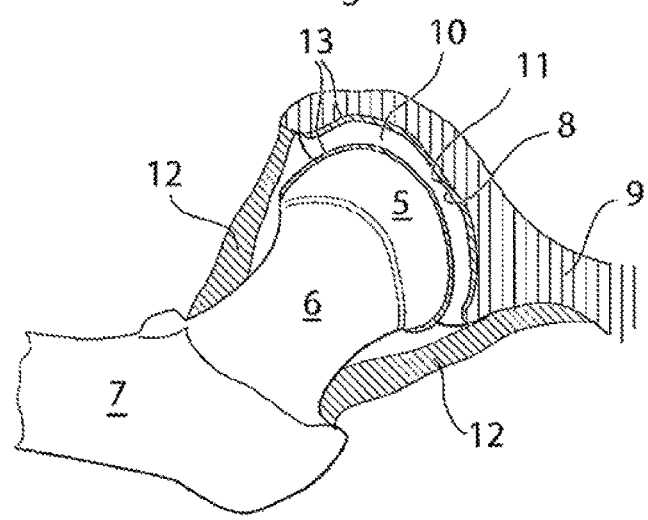
FIG. 2 shows the hip joint in section.

FIG. 2 shows the hip joint of a human patient in a lateral view. The hip joint comprises a caput femur 5 placed at the very top of collum femur 6 which is the top part of the femur bone 7. The caput femur is in connection with the acetabulum 8 which is a bowl shaped part of the pelvic bone 9. Both the caput femur surface 10 and the acetabulum surface 11 is covered with articular cartilage 13 which acts as a cushion in the hip joint. In patients with hip joint osteoarthritis, this articular cartilage 13 is abnormally worn down due to a low grade inflammation. The hip joint is surrounded by the hip joint capsule 12 which provides support for the joint and hinders luxation. After conventional hip joint surgery, penetrating the hip joint capsule 12, the capsule 12 is dramatically weakened due to the limited healing possibilities of its ligament tissue. By performing hip joint surgery without damaging the hip joint capsule 12 the patient can fully recover and place equal amount of strain on an artificial joint as is possible on a natural one.

Figure 3:
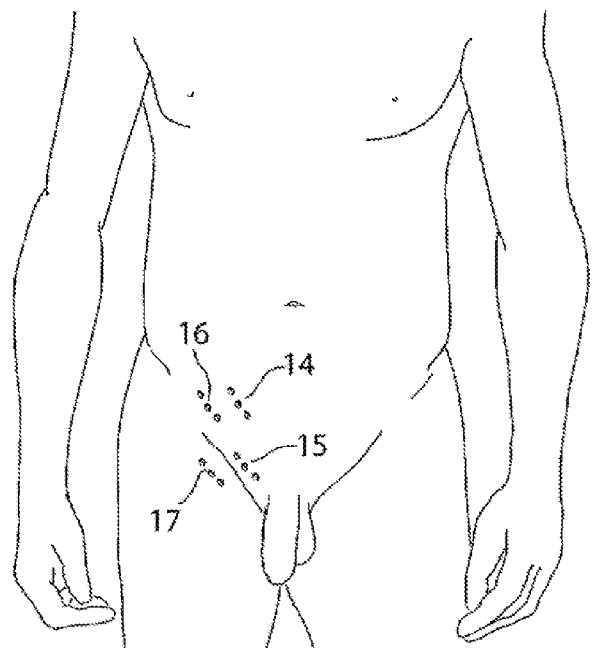
FIG. 3 shows different locations where small incisions can be made in the human body in the laparoscopic/arthroscopic method.

FIG. 3 shows a frontal view of the body of a human patient. A laparoscopic/arthroscopic method of operating the hip joint, from the opposite side from acetabulum, is according to a first embodiment performed starting with making small incisions 14 in the abdominal wall of the human patient. The small incisions enable the surgeon to insert laparoscopic/arthroscopic trocars into the abdomen of the human patient. According to the first embodiment the incisions 14 passes through the rectus abdominis and peritoneum in to the abdomen of the human patient. According to a second preferred embodiment the small incisions 15 is conducted through the rectus abdominis and in to the pelvic area, below peritoneum.

According to a third embodiment the small incisions 16 is performed just between Illium and the surrounding tissue, an incision 16 which could enable the pelvic bone to be dissected with very little penetration of fascia and muscular tissue. According to a fourth embodiment the incision 17 is made in the inguinal channel. In all of the four embodiments the tissue surrounding the pelvic bone 9 in the area opposite to acetabulum 8 is removed or penetrated which enables the surgeon to reach the pelvic bone 9.

Figure 4:
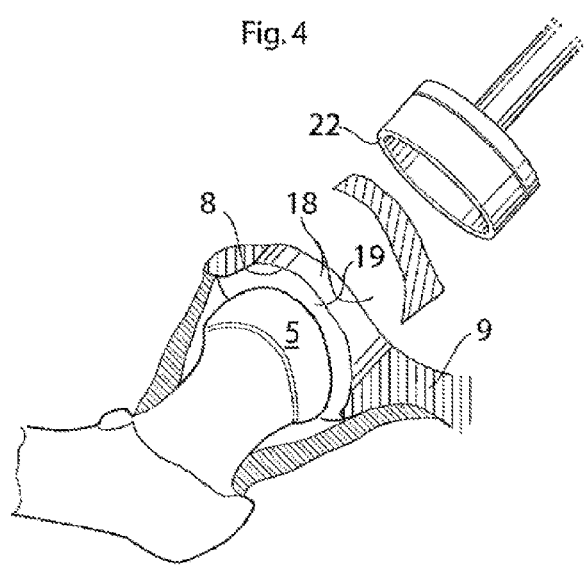
FIG. 4 shows the hip joint in section when a hole is created in the pelvic bone.
Figure 5:
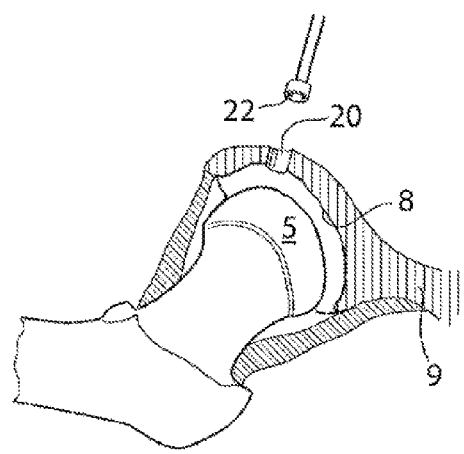
FIG. 5 shows the hip joint in section when a small hole is created in the pelvic bone.

After dissecting the pelvic bone 9 a hole 18 is created in the bone 9, shown in FIG. 4. The hole 18 passes through the pelvic bone from the opposite side from acetabulum 8 and into the hip joint 19. According to a first embodiment the hole 18 is large which allows a prosthesis to pass through said hole 18 in its full functional size. According to a second embodiment the hole 20 created in the surgical or laparoscopic/arthroscopic method is much smaller as shown in FIG. 5 allowing the surgical instrument creating the hole to be smaller, and thus the incision and dissection performed in the human body.

Figure 6:
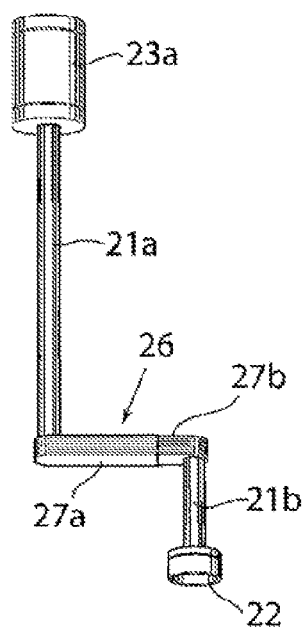
FIG. 6 shows the instrument that creates a hole in the pelvic bone according to a first embodiment.
Figure 7:
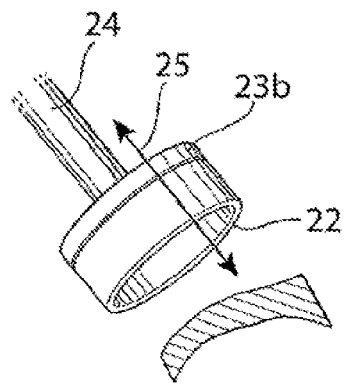
FIG. 7 shows the instrument that creates a hole in the pelvic bone according to a first embodiment in greater detail.

FIG. 6 shows a first embodiment of said surgical instrument creating the hole 18, 20 in the pelvic bone 9. The surgical instrument comprises a driving member 21a,b. The driving member 21a,b could be a shaft, a rod, a belt, a chain or any other element suitable for transferring force or torque. The surgical instrument also comprises a bone contacting organ 22 which is adapted to create the hole 18, 20 in the pelvic bone 9. The bone contacting organ 22 could have a sawing, drilling or milling effect using sharp objects; it is furthermore conceivable that said bone contacting organ 22 creates a hole using water, abrasive fluids, laser or radiation. The surgical instrument also comprises an operating device 23a adapted to operate the driving member 21a,b. The operating device could comprise an electrical, mechanical, pneumatic or magnetic motor and it could be adapted to create a rotating, oscillating, vibrating or repetitive movement. According to one embodiment the operating device 23b could be placed in direct connection with the bone contacting organ 22 shown in FIG. 7 in which case the operating device 23b also serves as driving member. In this construction a handle portion 24 could be attached to the surgical instrument facilitating the surgeons handling of said surgical instrument. To improve the reach of the surgical instrument the handle portion 24 could be attached perpendicular to the hole-creating direction 25 of the surgical instrument, it is furthermore conceivable that the handle portion 24 is bent by means of a parallel displaced part or section, a fixed angle, an adjustable angle or a flexible part or section.

According to one embodiment of FIG. 6 the surgical instrument further comprises a parallel displaced part or section 26. The parallel displaced part or section 26 improves the reach of the medical device and enables the creation of a hole 18 in the pelvic bone 9 from the opposite side from acetabulum 8. According to one embodiment shown in FIG. 6 the parallel displaced part or section 26 has a telescopic function by means of the parallel displaced part or section 26 being divided in to a first and second part 27a, b, wherein the second part 27b can slide in and out of the first part 27a.

Figure 8:
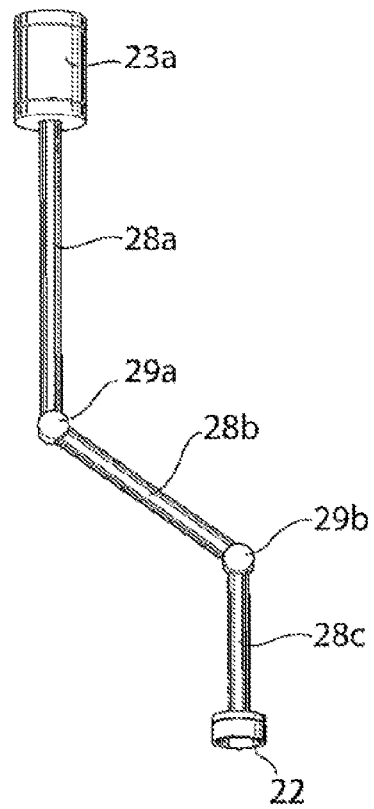
FIG. 8 shows the instrument that creates a hole in the pelvic bone according to a second embodiment.

FIG. 8 shows the surgical instrument according to a second embodiment wherein said surgical instrument comprises a driving member 28a,b,c with two angle adjusting members 29a,b. The angle adjusting members 29a,b could be adjustable for varying the angle of said driving member 28a,b,c or fixed in an angle suitable for creating a hole in the pelvic bone 9 from the opposite side from acetabulum 8. In another embodiment (not shown) the part of the driving member 28c in connection with the bone contacting organ 22 could be very short enabling the surgical instrument to operate very close to the pelvic bone 9 when creating a hole 18 in said pelvic bone 9.

Figure 9:
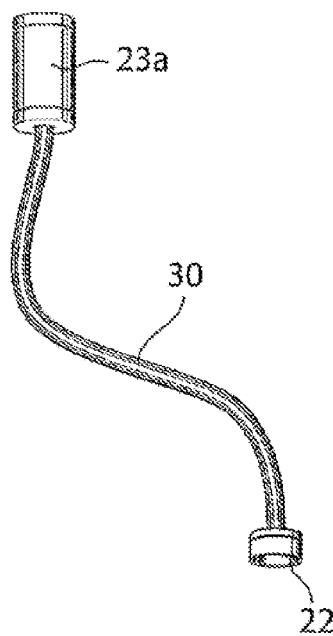
FIG. 9 shows the instrument that creates a hole in the pelvic bone according to a third embodiment.

FIG. 9 shows the surgical instrument according to a third embodiment wherein the driving member 30 is flexible, enabling said driving member 30 to be very precisely adjusted to create a hole 18 in the pelvic bone 9 of the patient. The stiffness of said driving member 30 could range from completely flexible to completely stiff to fit the surroundings of the particular operation.

FIG. 10 shows the bone contacting organ according to a first embodiment wherein the bone contacting organ 22a is adapted to crate a bone plug 31. The bone plug 31 could be adapted to be replaced into said hole 18 after the steps of the surgical or laparoscopic/arthroscopic method have been performed in the hip joint.

FIG. 11 shows the bone contacting organ according to a second embodiment wherein the bone contacting organ 22b is adapted to create small pieces of bone 32 when creating said hole 18 in the pelvic bone 9. The small pieces of bone could be transported from the area and out of the body using vacuum power or a hydraulic transport system.

FIG. 12 shows a frontal view of the body of a human patient, illustrating the laparoscopic/arthroscopic method of operating the hip joint from the opposite side from acetabulum 8. The hip joint comprising the acetabulum 8 and the caput femur 5. The small incisions 14 in the abdominal wall of the human patient allows the insertion of laparoscopic/arthroscopic trocars 33a,b,c into the body of the patients. Whereafter one or more camera 34, a surgical instrument adapted to create a hole in the pelvic bone 35, or instruments 36 for introducing, placing, connecting, attaching, creating or filling prosthesis or prosthetic parts, can be inserted into said body through said laparoscopic/arthroscopic trocars 33a,b,c.

Figure 13:
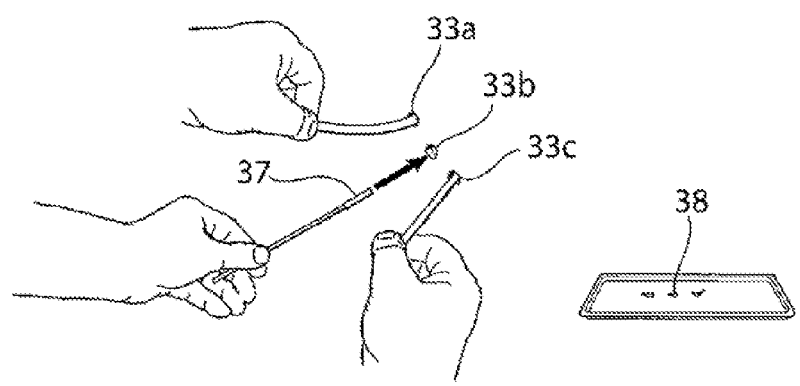
FIG. 13 shows a step of the laparoscopic/arthroscopic method in greater detail.

FIG. 13 shows a close-up of the insertion 37 of prosthetic parts 38 into the patients body through said laparoscopic/arthroscopic trocars 33a,b,c.

Figure 14:
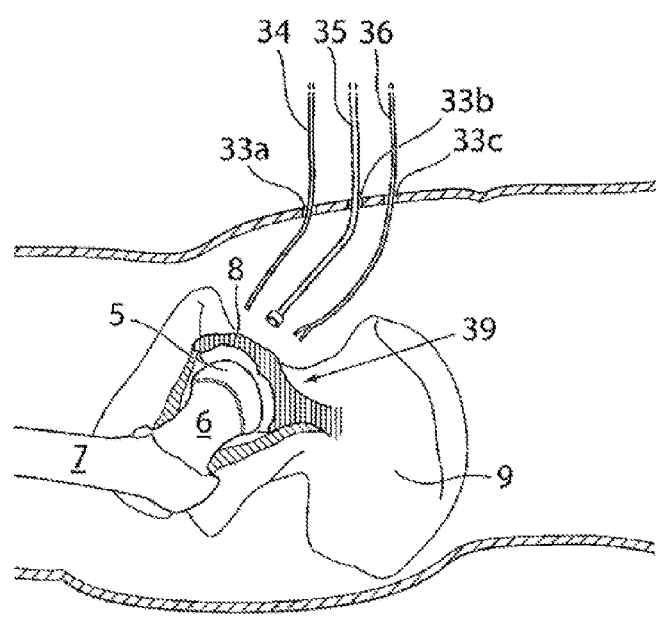
FIG. 14 shows a lateral view in section of the laparoscopic/arthroscopic method.

FIG. 14 shows a lateral view of the body of a human patient, with the hip joint shown in section. The hip joint comprises a caput femur 5 placed at the very top of collum femur 6 which is the top part of the femur bone 7. The caput femur 5 is in connection with the acetabulum 8 which is a bowl shaped part of the pelvic bone 9. Laparoscopic/arthroscopic trocars 33a,b,c is being used to reach the hip joint 39 with one or more camera 34, a surgical instrument 35 adapted to create a hole in the pelvic bone 9, or instruments 36 for introducing, placing, connecting, attaching, creating or filling prosthesis or prosthetic parts.

The surgical and laparoscopic/arthroscopic methods shown in FIGS. 1, 3, 12, 13, 14 further comprises the step of reaming the acetabulum 8 or the caput femur 5. According to a first embodiment the reaming of the acetabulum 8 or the caput femur 5 is performed using an expandable reamer shown in FIG. 15-17. The expandable reamer comprises at least one reaming blade 40 which comprises a reaming surface 41a,b. Said expandable reamer could be adapted to ream the acetabulum 8, the caput femur 5 or both. In the embodiment where said expandable reamer is adapted to ream the acetabulum 8 said reaming surface 41a is located on the exterior part of the at least one reaming blade 40, whereas in the embodiment when said expandable reamer is adapted to ream the caput femur 5, said reaming surface 41b is located on the interior part of the at least one reaming blade 40. According to a second embodiment said expandable reamer is adapted to ream both the acetabulum and the caput femur, in which case the reamer has reaming surfaces 41a,b both on the exterior and the interior part of the at least one reaming blade 40.

Figure 15:
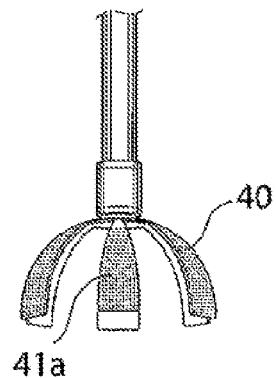
FIG. 15 shows the expandable reamer.
Figure 16:
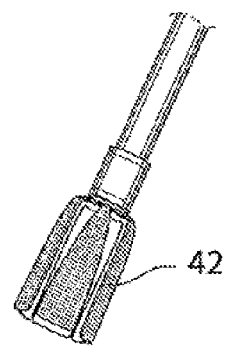
FIG. 16 shows the expandable reamer in its folded state.

FIG. 16 shows the expandable reamer according to a third embodiment, wherein the reaming blades 40 can be folded towards a center of the semi-sphere that the expandable reamer produces in its expanded state, shown in FIG. 15. The folding of the reaming blades 40 enables the expandable reamer to be introduced into a hip joint through a hole smaller than the area possible to ream using said expandable reamer.

Figure 17:
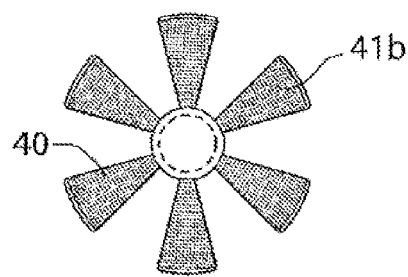
FIG. 17 shows the expandable reamer from underneath.

FIG. 17 shows the interior said of the expandable reamer with the reaming blades 40. In the embodiment when the expandable reamer is adapted to ream the caput femur said interior side of the at least one reaming blade 40 comprises a reaming surface 41b.

Figure 18:
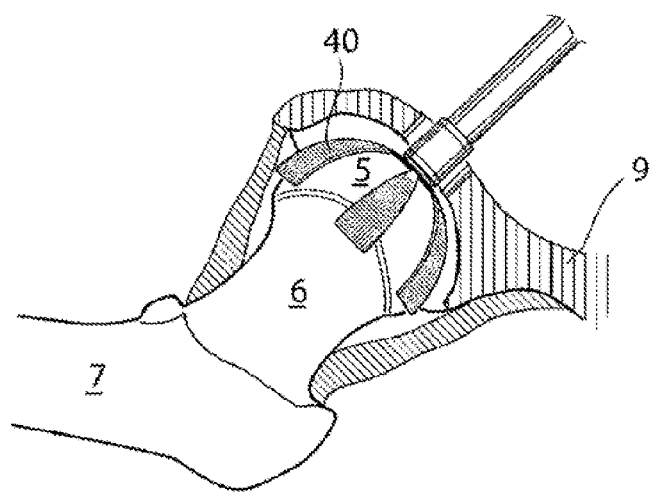
FIG. 18 shows the expandable reamer being used in the surgical or laparoscopic/arthroscopic method.

FIG. 18. shows the expandable reamer according to any of the embodiments when reaming said acetabulum 8 and/or said caput femur 5. The reamer can be adapted to be operated manually or by means of a rotating, vibrating or oscillating operating device.

According the one embodiment the bone contacting organ 22 of the surgical instrument shown in FIG. 6-11 can be replace with the expandable reamer shown in FIGS. 15-17, and in which case the expandable reamer can be powered using the operating device 23a,b used in said surgical instrument.

After the preparation of the hip joint surfaces the method step of inserting or creating new surfaces is performed.

Figure 19:
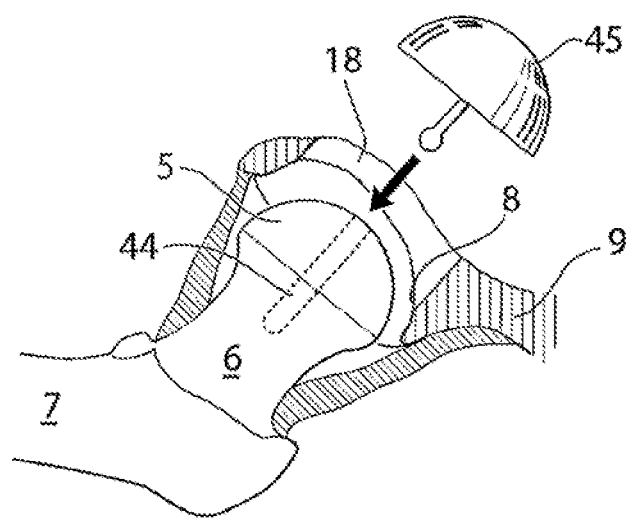
FIG. 19 shows the step of providing an artificial caput femur surface.

FIG. 19 shows the hip joint in section with the caput femur 5 placed at the very top of collum femur 6 which is the top part of the femur bone 7. The caput femur is in connection with the acetabulum 8 which is a bowl shaped part of the pelvic bone 9. According to a first embodiment the hole 18 created in the pelvic bone 9 from the opposite side from acetabulum 8, is larger than said artificial caput femur surface 45, enabling the insertion of said artificial caput femur surface 43 in its full functional size. Said insertion of said artificial caput femur surface 43 could be performed as a step of the surgical method, as well as a step of the laparoscopic/arthroscopic method. After the insertion, the artificial caput femur surface 43 is attached to the caput femur 5, according to the embodiment shown in FIGS. 19-20 the attaching is performed by means of a mechanical attachment 44 comprising a shaft or screw penetrating the cortex. It is however also conceivable that the mechanical attachment 44 is assisted by bone cement or adhesive placed between caput femur 5 and the artificial caput femur surface 43, or in connection with said shaft or screw 44. Alternative ways of attaching the artificial caput femur surface 43 includes: form fitting, welding, sprints, band or some other mechanical connecting member.

Figure 20:
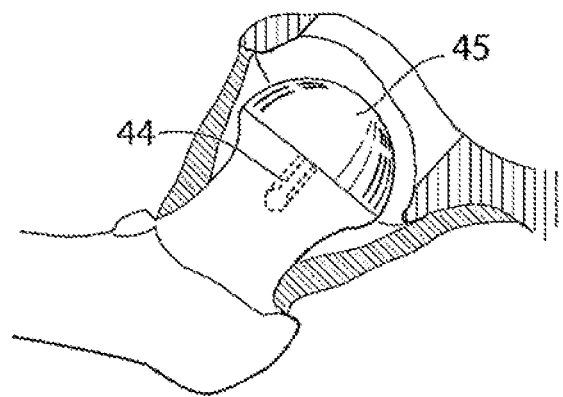
FIG. 20 shows the a section of the hip joint after the artificial caput femur surface has been provided, FIG. 21a show the insertion of artificial caput femur surface parts into the hip joint.

FIG. 20 shows the hip joint in section with the artificial caput femur surface 43 attached to the caput femur 5.

Figure 21:
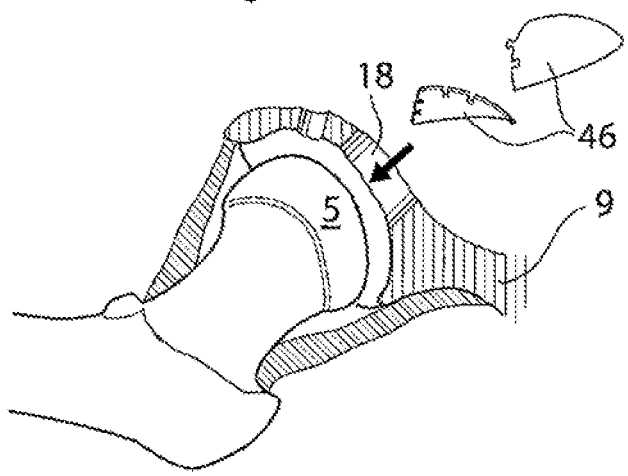
FIG. 21b shows the artificial caput femur surface parts after they have been connected inside of the hip joint forming an artificial caput femur surface.
FIG. 21c shows how the form of the artificial caput femur surface parts enables the connection of the artificial caput femur surface parts to form an artificial caput femur surface.
FIG. 21d shows a camera being inserted into the hip joint.
Figure 21:
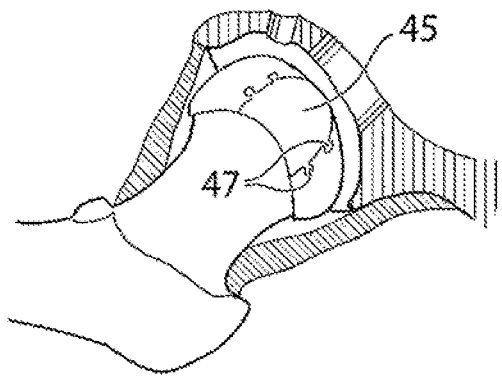
Figure 21:
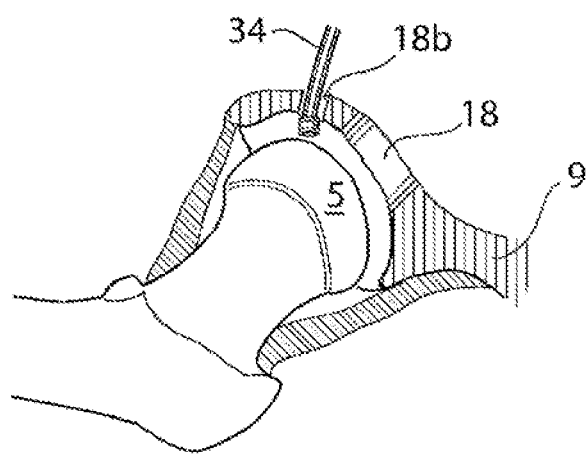
Figure 21:
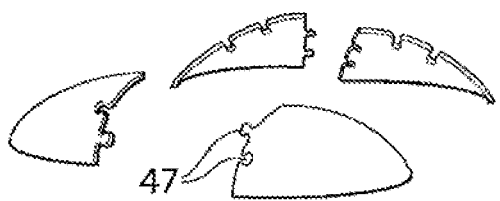

FIG. 21a shows the hip joint in section according to a second embodiment in which the hole 18 in the pelvic bone 9 is smaller than the artificial caput femur surface 45 in its full functional size. According to this embodiment the artificial caput femur surface 45 is introduced into said hip joint through the hole 18 in the pelvic bone 9 form the opposite side from acetabulum 8. The artificial caput femur surface parts 46 are connected to each other after insertion into said hip joint to form the artificial caput femur surface 45.

FIG. 21b shows the hip joint in section when the artificial caput femur surface parts 46 are connected to each other using form fitting 47, however it is conceivable that the form fitting is assisted or replaced with adhesive or bone cement. After the artificial caput femur surface parts 46 have been introduced and connected in the hip joint, they are mechanically fixated to the caput femur 5, the mechanical fixation could be done by means of screws, form fitting, welding, sprints, band, adhesive or some other mechanical attachment member.

FIG. 21c shows the artificial caput femur surface parts 46 with the parts supplying the form fitting 47.

FIG. 21d shows the hip joint in section wherein a second hole 18b in the pelvic bone 9 enables the surgeon to place a camera 34 into the hip joint, preferably used in the laparoscopic/arthroscopic method.

Figure 22:
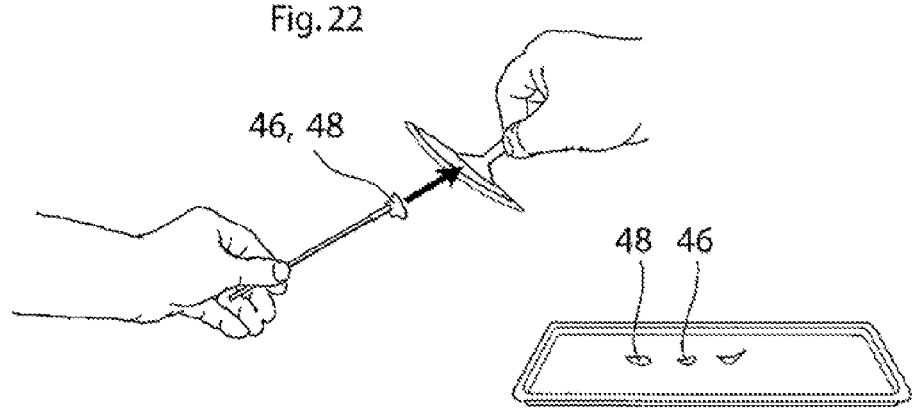
FIG. 22 shows the insertion of artificial hip joint surface parts in the surgical method.

FIG. 22 shows the artificial hip joint surface parts 48 being inserted through an incision according to the surgical method. According to a first embodiment the artificial hip joint surface parts 48 are artificial caput femur surface parts 46, adapted to be connected to each other after the insertion to form an artificial caput femur surface 45. The same insertion can be performed in the laparoscopic/arthroscopic method, shown in FIG. 13.

Figure 23:
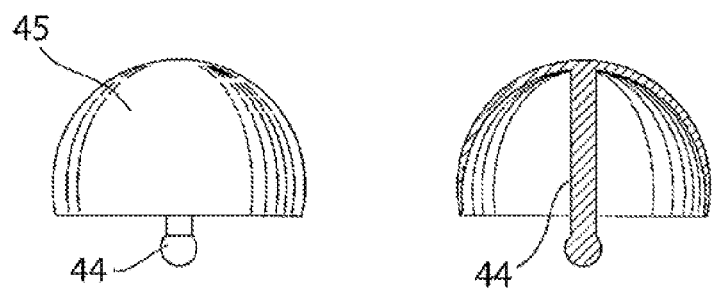
FIG. 23 shows the artificial caput femur surface according to a first embodiment.

FIG. 23 shows the artificial caput femur surface 45 according to a first embodiment also shown in FIG. 19-20. The shaft or screw placed in the middle of the artificial caput femur surface 45 serves as a mechanical attachment 44 penetrating the cortex of the caput femur 5 and fixating the artificial caput femur surface 45 to the caput femur 5.

Figure 24:
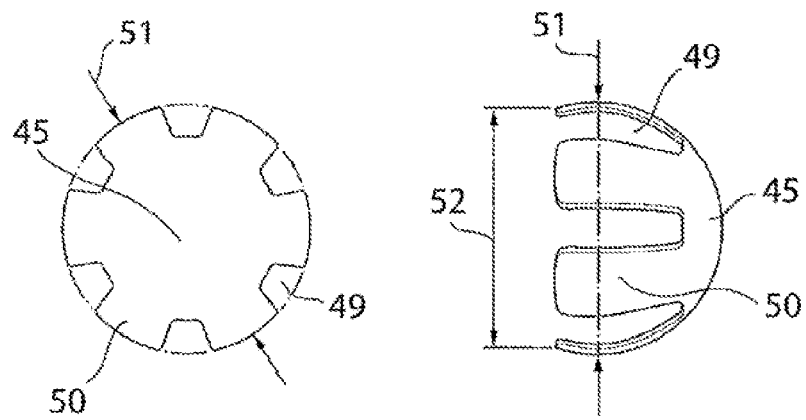
FIG. 24 shows the artificial caput femur surface according to a second embodiment.

FIG. 24 shows a second embodiment of the artificial caput femur surface 45. The second embodiment comprises at least one slit 49 enabling the construction of the artificial caput femur surface 45 to be flexible, thus enabling the largest diameter 51 to vary for insertion of said artificial caput femur surface 45 through a hole in the pelvic bone 9 smaller than the full functional size of said artificial caput femur surface 45. According to this embodiment the artificial caput femur surface 45 further comprises artificial caput femur surface arms 50 located on the sides of said at least one slit 49. The caput femur surface arms 50 can be made of a flexible material enabling the insertion through a hole 18 in the pelvic bone 9 smaller than the largest diameter 51 of said artificial caput femur surface 45 when in its full functional size.

According to one embodiment the artificial caput femur surface 45 could be adapted to pass beyond the maximum diameter of the caput femur 5. This enables a mechanical fixation using the form of said artificial caput femur surface 45. In the embodiment where the artificial caput femur surface 45 travels beyond the maximum diameter of the caput femur 5 the construction can be made flexible so that the size of the artificial caput femur surface 45 can vary to become smaller for insertion through a hole 18 in the pelvic bone smaller than the full functional size of the artificial caput femur surface 45, and have an opening adapter to travel over the caput femur 5 that can be larger that the same opening is in the full functional size of the artificial caput femur surface 45 enabling the artificial caput femur surface 45 to at least partly cover an area beyond the maximum diameter of caput femur 5 from the direction of the acetabulum 8. According to a second embodiment the artificial caput femur surface 45 comprises two or more artificial caput femur surface arms 50 which have a cross sectional distance 52 between each other. This cross sectional distance 52 is according to one embodiment shorter than the maximum diameter of the caput femur 5 enabling the mechanical fixation of the artificial caput femur surface 45 by means of said artificial caput femur surface arms 50.

Figure 25A:
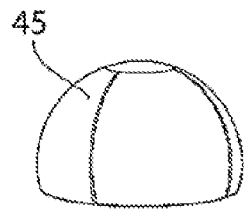
FIG. 25a shows the artificial caput femur surface according to a third embodiment.
Figure 25B:
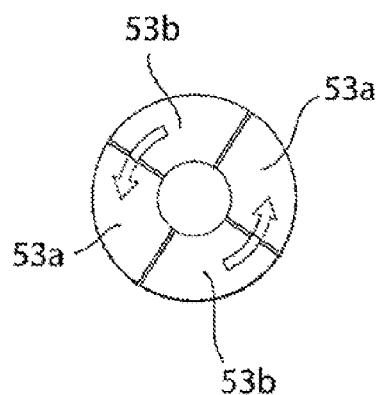
FIG. 25b shows the function of the artificial caput femur surface according to a third embodiment.
Figure 25C:
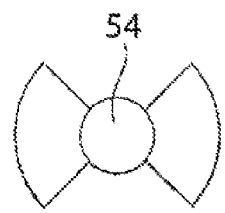
FIG. 25c shows the artificial caput femur surface according to a third embodiment, in its folded state.
Figure 25D:
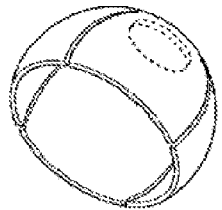
FIG. 25d shows the artificial caput femur surface according to a third embodiment in perspective.
Figure 25E:
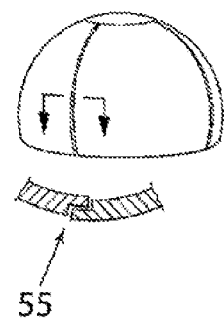
FIG. 25e shows the connecting function of the artificial caput femur surface according to a third embodiment.

FIG. 25a,b,c,d,e shows the artificial caput femur surface 45 according to a fourth embodiment, in which said artificial caput femur surface 45 comprises a first 53a and a second 53b section, as shown in FIG. 25b. The first and second sections are displaceable in relation to each other. According to a first embodiment said first section 53a can be rotated in relation to said second section 53b so that said second section 53b travels underneath said first section 53a to create a displaced artificial caput femur surface 54, as shown in FIG. 25c, which is possible to insert into a hip joint of a human patient through a hole 18 being oval, or at least having an area smaller than the cross sectional area of the artificial caput femur surface 45 when in its full functional size 45, as shown in FIG. 25a. According to this embodiment the two sections are connected to each other when the artificial caput femur surface 45 is returned to its full functional size using a mechanical form fitting 55, as shown in FIG. 25e. However it is also conceivable that said connection is assisted or replaced with screws, welding, sprints, band, adhesive or some other mechanical connecting member.

Figure 26A:
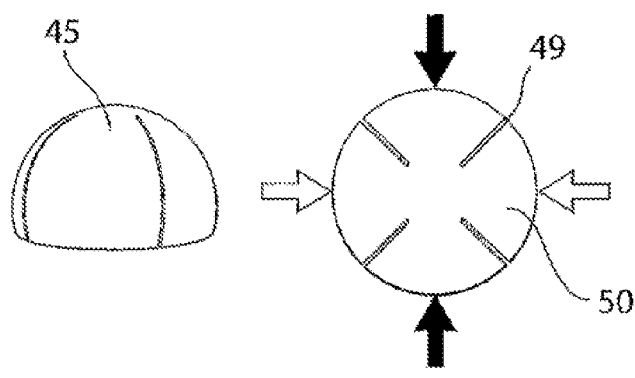
FIG. 26a shows the artificial caput femur surface according to a fourth embodiment.

FIG. 26 shows a fourth embodiment of an artificial caput femur surface 45 comprising four slits. The artificial caput femur surface 45 is flexible in its construction allowing the four artificial caput femur arms 50 to be folded towards the center axis of the artificial caput femur surface 45 thus allowing the artificial caput femur surface 45 to be inserted into a hip joint through a hole smaller than the full functional size of the artificial caput femur surface 45. The artificial caput femur surface 45 according to this embodiment can be constructed to go beyond the maximum diameter of the caput femur 5, in which case the construction with the slits 49 allows the artificial caput femur surface 45 to change to both a smaller and a larger size than said full functional size.

Figure 26B:
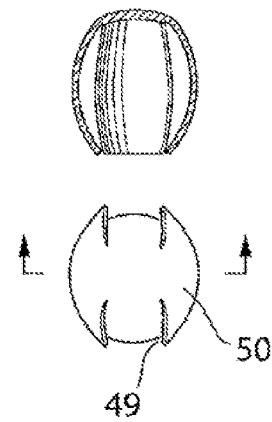
FIG. 26b shows the artificial caput femur surface according to the fourth embodiment in its folded state.

FIG. 26b shows the artificial caput femur surface 45 in section when said artificial caput femur surface arms 50 are folded for insertion through a hole 18 with an area smaller than the largest area of the artificial caput femur surface 45 when in its full functional size.

FIG. 27a shows fifth embodiment of the artificial caput femur surface 45 having multiple artificial caput femur surface parts 46. Said multiple artificial caput femur surface parts 46 are adapted to be connected to an interconnecting artificial caput femur surface part 56 after insertion into a hip joint. The interconnecting artificial caput femur surface part 56 comprises self locking connecting members 57, shown in FIG. 27b, that fits with corresponding self locking members 58 of the artificial caput femur surface parts 46. The artificial caput femur surface parts 46 creates an artificial caput femur surface 45 when connected to each other, shown in FIG. 27c. The self locking members 57,58 can be assisted or replaced with screws, welding, sprints, band, adhesive or some other mechanical connecting member. The artificial caput femur surface 45 according to this embodiment can further be adapted to go beyond the maximum diameter of the caput femur 5.

FIG. 28*a* shows a sixth embodiment the artificial caput femur surface 45 adapted to pass beyond the maximum diameter of the caput femur 5. This enables a mechanical fixation using the form of said artificial caput femur surface 45. In this embodiment the artificial caput femur surface 45 comprises at least two slits 49 adapted to make said artificial caput femur surface 45 flexible for travelling over and beyond the maximum diameter of the caput femur 5. The construction could further be made flexible so that the size of the artificial caput femur surface 45 can vary to become smaller for insertion through a hole 18 in the pelvic bone 9 smaller than the full functional size of the artificial caput femur surface 45. It is also conceivable that the artificial caput femur surface 45 comprises two or more artificial caput femur surface arms 50 which have a cross sectional distance 52 between each other. This cross sectional distance 52 is according to one embodiment shorter than the maximum diameter of the caput femur 5 enabling the mechanical fixation of the artificial caput femur surface 45 by means of said artificial caput femur surface arms 50. For further fixation a band, cord or wire 59 can be placed around the artificial caput femur surface 45 beyond the maximum diameter of the caput femur 5. The band, cord or wire can be mechanically connected using a self locking member 60 for forming a ring-shaped element able to assist in the fixation of the artificial caput femur surface 45 to the caput femur 5.

FIG. 28*b* shows the artificial caput femur surface 45 when fixated to the caput femur with the supporting band, cord or wire placed around the artificial caput femur surface 45 beyond the maximum diameter of the caput femur 5.

FIG. 28*c* shows the artificial caput femur surface 45 in section having a greatest cross-sectional distance 52 adapted to travel over and beyond the maximum diameter of the caput femur 5. The maximum diameter of the caput femur 5 being positioned at a corresponding largest cross sectional distance 61 of the artificial caput femur surface A second distance 62 is the distance that the artificial caput femur surface 45 travels beyond the maximum diameter of the caput femur 5. Said distance 62 being part of the mechanical fixation of the artificial caput femur surface 45 to the caput femur 5.

Figure 29:
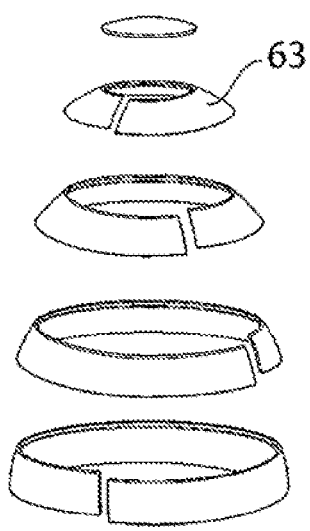
FIG. 29a shows the artificial caput femur surface according to a seventh embodiment.
FIG. 29b shows the artificial caput femur surface according to the seventh embodiment when assembled.
FIG. 29c shows the artificial caput femur surface according to the seventh embodiment with the connecting members enlarged.
Figure 29:
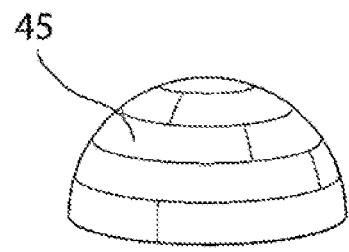
Figure 29:
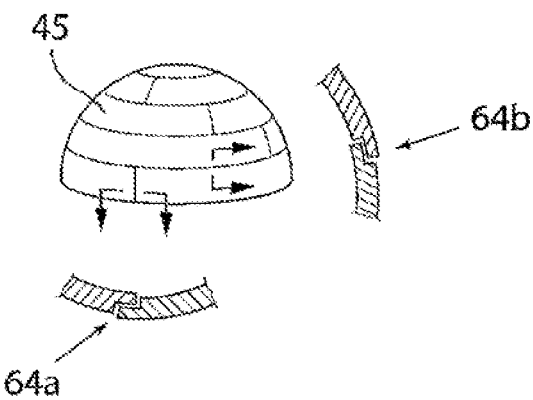

FIG. 29*a* shows a seventh embodiment of the artificial caput femur surface 45 comprising multiple ring-shaped artificial caput femur surface parts 63. Said multiple ring-shaped artificial caput femur surface parts 63 are adapted to be connected to each other to form an artificial caput femur surface 45. According to one embodiment said artificial caput femur surface parts 63 are adapted to be connected to each other using mechanical connecting members 64*a,b*, 64*a* shows how an individual ring-shaped artificial caput femur surface part 63 can be connected to itself to form a continuous ring shape 64*b* shows how an individual ring-shaped artificial caput femur surface part 63 connects to other ring-shaped artificial caput femur surface parts 63 to form an artificial caput femur surface 45. The artificial caput femur surface 45 according to this embodiment can further be adapted to go beyond the maximum diameter of the caput femur 5.

After the step of providing an artificial caput femur surface the surgical and laparoscopic/arthroscopic methods could further comprises the step of providing an artificial acetabulum surface.

Figure 30:
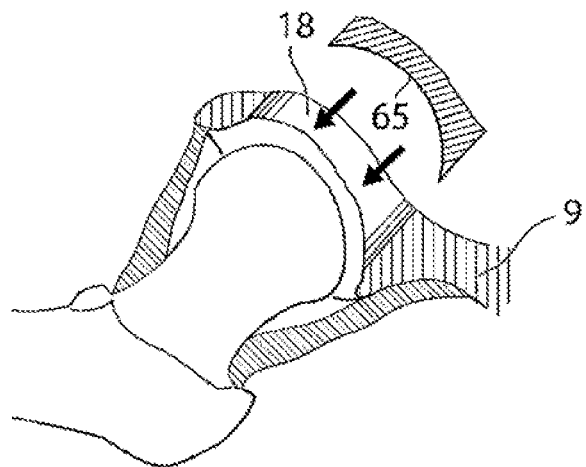
FIG. 30 shows an artificial acetabulum surface when being inserted into a hip joint.

According to a first embodiment the artificial acetabulum surface 65 is provided through a hole 18 in the pelvic bone 9 from the opposite side from acetabulum 8. FIG. 30 shows an artificial acetabulum surface 65 in its full functional size as it is being inserted through a hole 18 in the pelvic bone 9.

FIG. 31 shows an artificial acetabulum surface 65 according to a second embodiment in which the artificial acetabulum surface 65 comprises at least one slit 66 enabling the artificial acetabulum surface 65 to vary in size for insertion through a hole 18 in the pelvic bone 9 smaller than the full functional size of the artificial caput femur surface 45. The slits 66 are placed between one or more artificial caput femur surface arms 67 which are flexible by means of the material or by means of a joint affecting said artificial caput femur surface arms 67.

FIG. 32*a,b,c* shows an artificial acetabulum surface 65 according to a second embodiment in which the artificial acetabulum surface 65 comprises multiple artificial acetabulum surface parts 68. Said multiple artificial acetabulum surface parts 68 are adapted to be connected to an interconnecting artificial acetabulum surface part 69 after insertion into a hip joint. The interconnecting artificial caput femur surface part 69 comprises self locking connecting members 70*a*, shown in FIG. 32*b*, that fits with corresponding self locking members 70*b* of the artificial acetabulum surface parts 68. The artificial acetabulum surface parts 68 create an artificial acetabulum surface 65 when connected to each other, shown in FIG. 32*c*. The self locking members 70*a,b* can be assisted or replaced with screws, welding, sprints, band, adhesive or some other mechanical connecting member.

FIG. 33*a,b,c* shows an artificial acetabulum surface 65 according to a third embodiment in which the artificial acetabulum surface 65 comprises multiple ring-shaped artificial acetabulum surface parts 71. Said multiple ring-shaped artificial acetabulum surface parts 71 are adapted to be connected to each other to form an artificial acetabulum surface 65 after insertion in a hip joint. According to one embodiment said artificial acetabulum surface parts 71 are adapted to be connected to each other using mechanical connecting members 72*a,b*.

FIG. 33*c* shows how an individual ring-shaped artificial acetabulum surface part 72*a* can be connected to itself using the mechanical connecting member 70*a* to form a continuous ring shape. Further 33*c* shows how an individual ring-shaped artificial acetabulum surface part 71 connects to other ring-shaped artificial acetabulum surface parts 63 using the mechanical connecting member 72*b* to form an artificial acetabulum surface 65.

Figure 34:
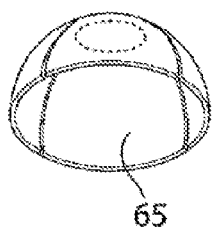
FIG. 34a shows an artificial acetabulum surface according to a fourth embodiment.
FIG. 34b shows the function of the artificial acctabulum surface according to the fourth embodiment.
FIG. 34c shows an artificial acetabulum surface according to a fourth embodiment in its folded state.
FIG. 34d shows the connection function of the artificial acetabulum surface according to the fourth embodiment.
Figure 34:
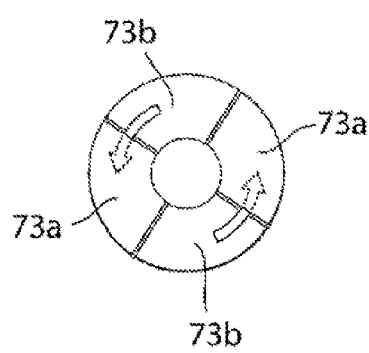
Figure 34:
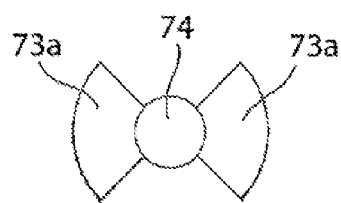
Figure 34:
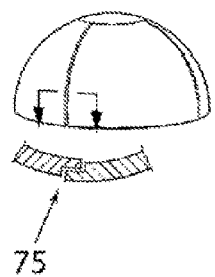

FIG. 34*a,b,c,d* shows an artificial acetabulum surface 65 according to a fourth embodiment in which the artificial acetabulum surface 65 comprises a first 73*a* and a second 73*b* section, shown in FIG. 34*b*. The first and second sections are displaceable in relation to each other. According to a first embodiment said first section 73*a* can be rotated in relation to said second section 73*b* so that said second section 73*b* travels underneath said first section 73*a* to create a displaced artificial acetabulum surface 74, as shown in FIG. 34*c*, which is possible to insert into a hip joint of a human patient through a hole being oval, or at least having an area smaller than the cross sectional area of the artificial acetabulum surface 65 when in its full functional size 65.

According to this embodiment the two sections 73*a,b* are connected to each other when the artificial acetabulum surface is returned to its full functional size using a mechanical form fitting 75, as shown in FIG. 34*d*. However it is also conceivable that said connection is assisted or replaced with screws, welding, sprints, band, adhesive or some other mechanical connecting member.

Figure 35:
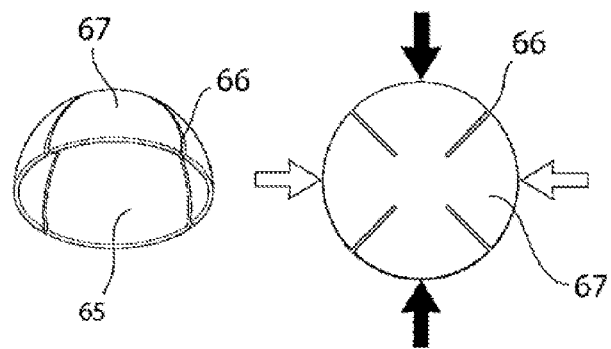
FIG. 35a shows an artificial acetabulum surface according to a fifth embodiment.
FIG. 35b shows an artificial acetabulum surface according to the fifth embodiment in its folded state.
Figure 35:
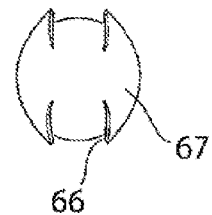

FIG. 35*a* shows an artificial acetabulum surface 65 according to a fifth embodiment in which the artificial acetabulum surface 65 comprises four slits 66. The artificial acetabulum surface 65 is flexible in its construction allowing the four artificial acetabulum arms 67 to be folded towards the center axis of the artificial acetabulum surface 65 thus allowing the artificial acetabulum surface to be inserted into a hip joint through a hole smaller than the full functional size of the artificial acetabulum surface 65.

FIG. 35*b* shows the artificial acetabulum surface 65 according to the fifth embodiment in its folded state.

Figure 36:
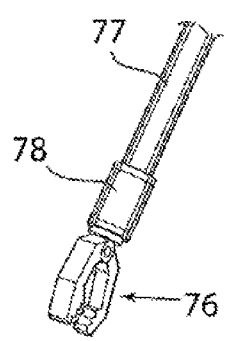
FIG. 36a shows an instrument for inserting parts into a hip joint according to a first embodiment.
FIG. 36b shows an instrument for inserting parts into a hip joint according to a second embodiment.
FIG. 36c shows an instrument for inserting parts into a hip joint according to a third embodiment.
Figure 36:
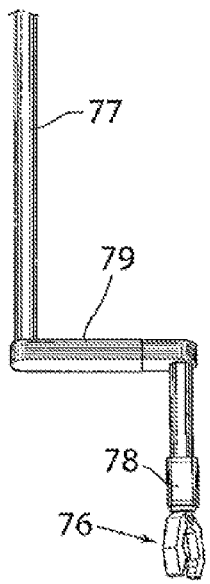
Figure 36:
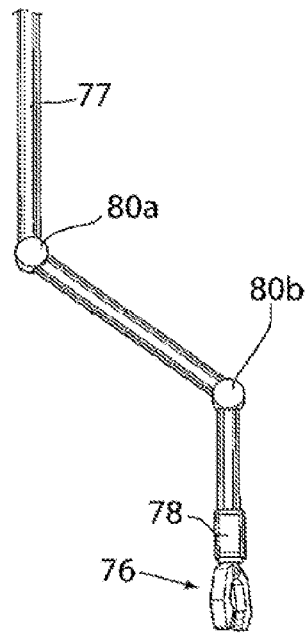

FIG. 36*a* shows a surgical instrument adapted to insert a prosthesis, prosthetic parts or parts needed to create or provide a hip joint surface, according to a first embodiment. The surgical instrument comprises a gripping portion 76 and a handling portion 77. According to the embodiments shown in FIG. 36*a,b,c* the instrument further comprises a rotation element 78 that enables the gripping part 76 to rotate in relation to the handling part 77, however it is equally conceivable that the surgical instrument lacks this rotation element 78.

FIG. 36*b* shows the surgical instrument adapted to insert a prosthesis, prosthetic parts or parts needed to create or provide a hip joint surface, according to a second embodiment. According to this embodiment the surgical instrument further comprises a parallel displaced section 79, which increases the reach of the instrument and facilitates the reaching of the hip joint through a hole in the pelvic bone from the opposite side from acetabulum.

FIG. 36*c* shows the surgical instrument adapted to insert a prosthesis, prosthetic parts or parts needed to create or provide a hip joint surface, according to a third embodiment. According to this embodiment the surgical instrument further comprises two angle adjusting members 80*a,b*. The angle adjusting members could be adjustable for varying the angle of said gripping part 76 in relation to the handling portion 77, or fixed in an angle suitable for creating operating in a hip joint through a hole in the pelvic bone from the opposite side from acetabulum 8.

Figure 37:
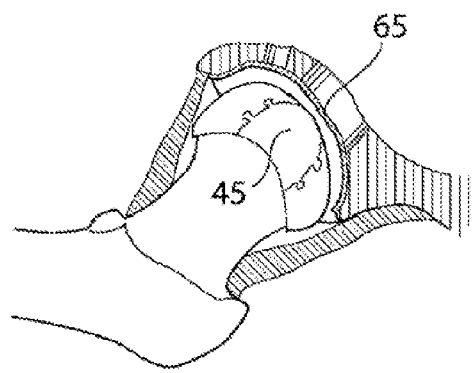
FIG. 37 shows a hip joint in section after an artificial caput femur surface and an artificial acetabulum surface have been provided.

FIG. 37 shows the hip joint in section after the artificial caput femur surface 45, and the artificial acetabulum surface 65 have been provided.

A different approach to the step of providing an artificial hip joint surface will now be described. This approach comprises the steps of casting an artificial hip joint surface inside of the hip joint. These steps can be performed by means of a mould, or without.

Figure 38:
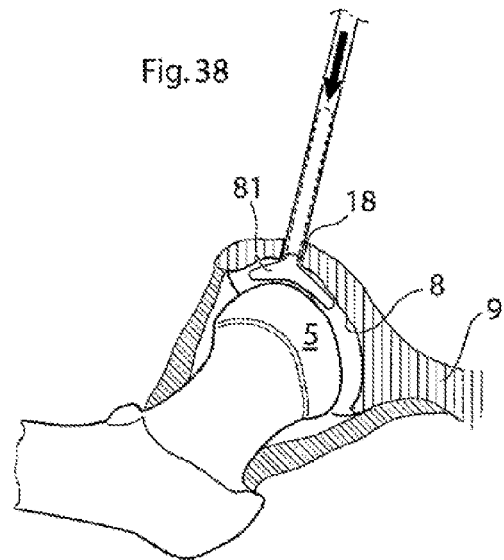
FIG. 38 shows a hip joint in section when a mould is being inserted.

FIG. 38 shows the step of placing a mould 81 inside of the hip joint of a human patient through a hole 18 in the pelvic bone 9. The step of placing said mould 81 can be performed in the surgical, or in the laparoscopic/arthroscopic method.

Figure 39:
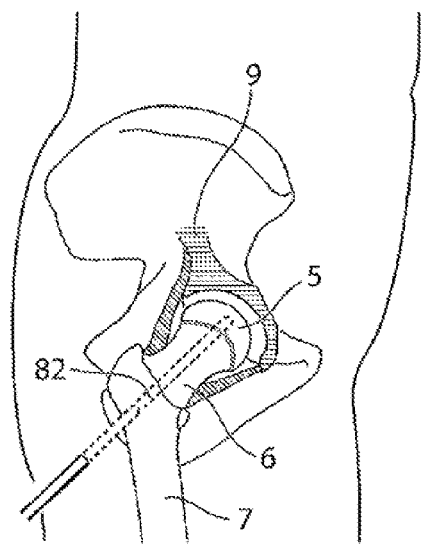
FIG. 39a shows the creation of a hole in the femur bone.
FIG. 39b shows an instrument able to introduce objects into a hip joint through the femur bone.
FIG. 39c shows the placing of a mould inside of the hip joint using an instrument that operates through the femur bone.
FIG. 39d shows the hip joint in section after the placing of a mould inside of the hip joint using an instrument that operates through the femur bone.
Figure 39:
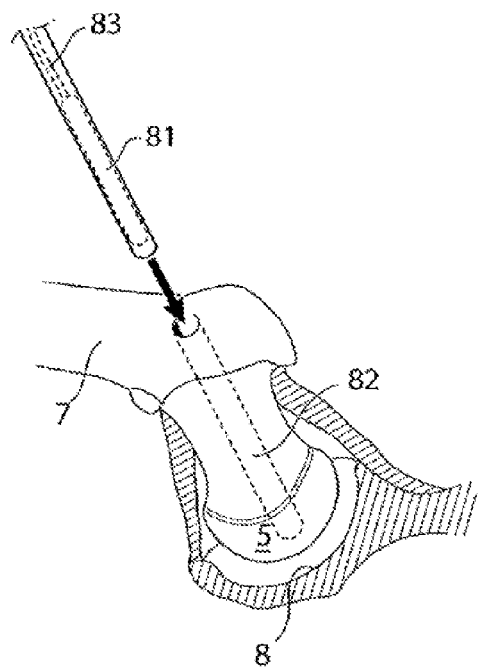
Figure 39:
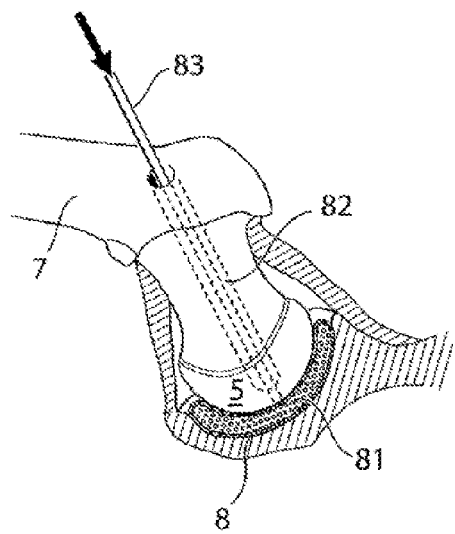
Figure 39:
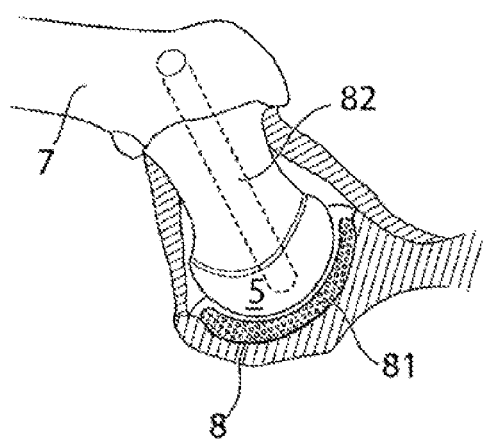

FIG. 39*a,b,c,d* shows an alternative approach to placing said mould 81 in the hip joint of a human patient. Said alternative approach comprises the steps of creating a hole 82 in the femur bone 7 following a length axis of the collum femur 6, said hole starting from the lateral side of the thigh, penetrating the cortex of the femur bone 7 and eventually reaching the cortex of the caput femur 5 from the inside thereof, penetrating said cortex and entering into the hip joint. After the creation of the hole 82 in the femur bone 7 the mould 81 is inserted into the hip joint through the hole 82 using a surgical instrument 83 adapted therefor, shown in FIG. 39*b*.

FIG. 39*c* shows the mould 82 when being inserted into the hip joint using the surgical instrument 83 adapted therefor.

FIG. 39*d* shows the mould 82 after insertion into the hip joint, the surgical instrument used to place said mould 82 in the hip joint is retracted after the insertion is completed.

It is also conceivable that the hip joint surface is provided by casting the hip joint surface inside of the hip joint without the use of a mould.

Figure 40:
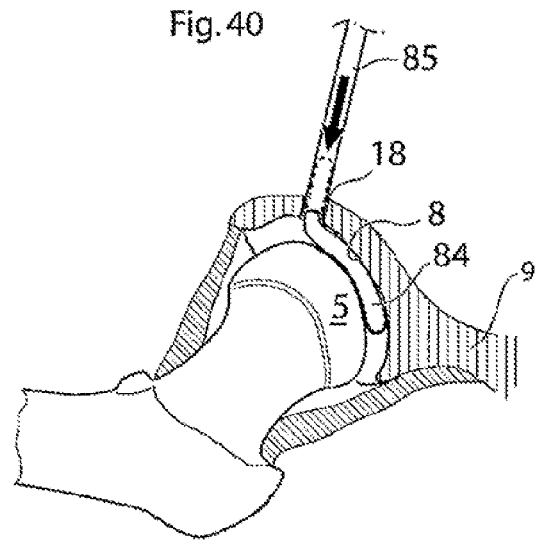
FIG. 40 shows the insertion of a first sealing member into a hip joint.

FIG. 40 shows the hip joint in section wherein a first sealing member 84 is inserted through a hole 18 in the pelvic bone 9 using an instrument adapted therefor 85. The step of placing said first sealing member 84 can be performed in the surgical, or in the laparoscopic/arthroscopic method.

Figure 41:
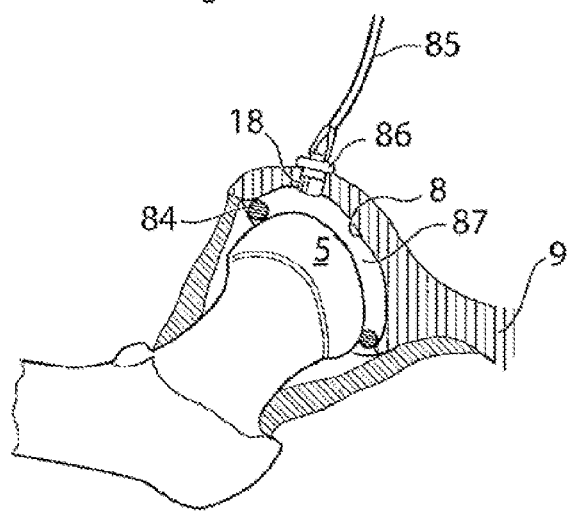
FIG. 41 shows the insertion of a second sealing member.

FIG. 41 shows the hip joint in section wherein a second sealing member 86 is inserted through the surgical or laparoscopic/arthroscopic method. The first 84 and second 86 sealing members creates a sealed space 87 between the acetabulum 8 and the caput femur 5 adapted to be used as a mould for providing an artificial acetabulum 65 and/or a caput femur surface 45.

Figure 42:
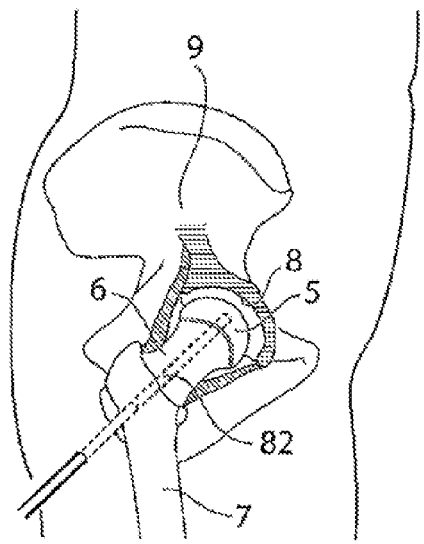
FIG. 42a shows the creation of a hole in the femur bone.
FIG. 42b shows an instrument able to introduce objects into a hip joint through the femur bone.
FIG. 42c shows the placing of a sealing member inside of the hip joint using an instrument that operates through the femur bone.
Figure 42:
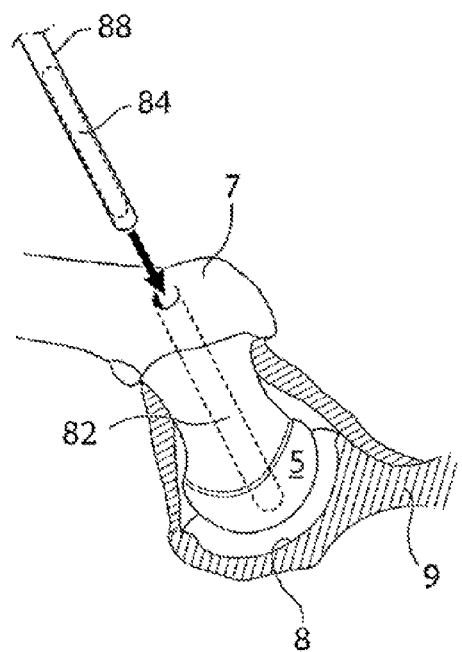
Figure 42:
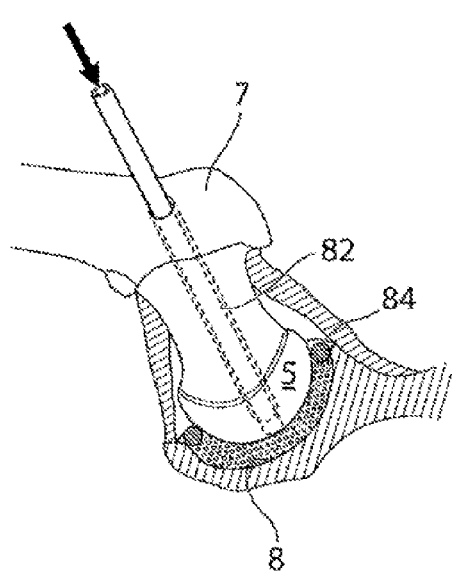

FIG. 42*a,b,c* shows an alternative approach to placing said first sealing member 84 in the hip joint of a human patient. Said alternative approach comprises the steps of creating a hole 82 in the femur bone 7 following a length axis of the collum femur 6, as shown in FIG. 44*a*, said hole starting from the lateral side of the thigh, penetrating the cortex of the femur bone 7 and eventually reaching the cortex of the caput femur 5 from the inside thereof, penetrating said cortex and entering into the hip joint. After the creation of the hole 82 in the femur bone 7 the first sealing member 84 is inserted into the hip joint through the hole 82 using a surgical instrument 88 adapted therefor, as shown in FIG. 44*c*.

FIG. 43*a,b,c* shows the surgical instrument adapted to insert a mould 81 and/or a first and second sealing member 84,86 into the hip joint of a human patient through a hole 18 in the pelvic bone 9 or a hole 82 in the femur bone 9.

FIG. 43*b* shows a section of the surgical instrument 83,85,88 comprising a tube like element for housing of the mould 81 and/or said first and second sealing members 84,86. A piston 89 used to transport said mould 81 and/or first and second sealing members 84,86 into the hip joint of a human patient is also shown.

FIG. 43*c* shows a surgical instrument 83,85,88 adapted to insert a mould 81 and/or a first and second sealing member 84,86 into the hip joint of a human patient, the second embodiment further comprises a flexible or bent part 91 improving the reach of the surgical instrument.

After the steps of providing a mould 81 or a sealed space 87, fluid is injected into said mould 81 or into said sealed space 87 through the hole 18 in the pelvic bone 9 or the hole 82 in the femur bone 7.

FIG. 44 shows a lateral section of the human body wherein an injecting member 92 injects a fluid into a mould 81 in the hip joint through a hole 18 in the pelvic bone 9 from the opposite side from acetabulum 8.

Figure 45:
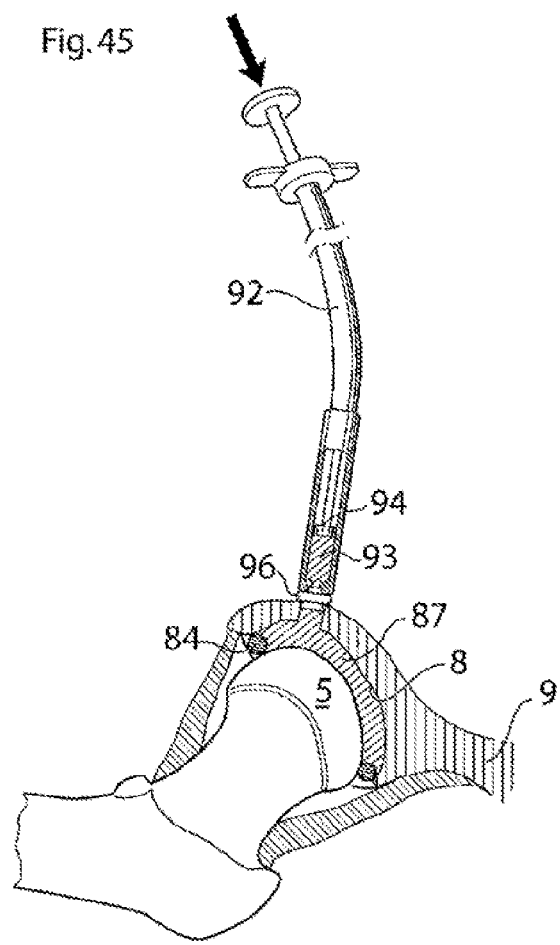
FIG. 45 shows the filling of a sealed area inside of the hip joint using an instrument that operates through the pelvic bone.

FIG. 45 shows the hip joint in section wherein an injecting member 92 injects a fluid 93 into a sealed area 87 in the hip joint through a hole 18 in the pelvic bone 9 from the opposite side from acetabulum 8. Said sealed area 87, being sealed by a first 84 and second 86 sealing member. The injecting member 92 comprises a piston 94 that pushes said fluid 93 into the sealed area 87.

Figure 46:
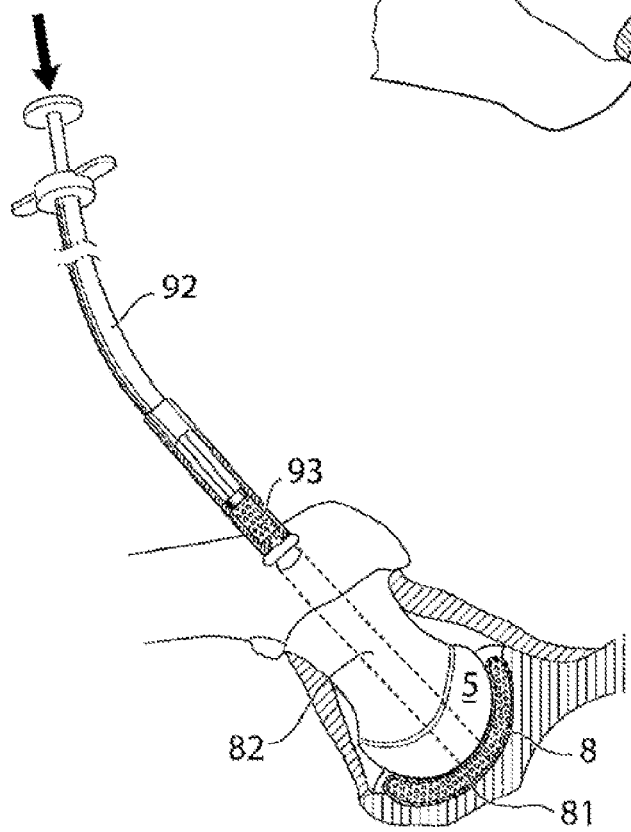
FIG. 46 shows the filling of a mould inside of the hip joint using an instrument that operates through the femur bone.

FIG. 46 shows the hip joint in section wherein an injecting member 92 injects a fluid 93 into a mould 81 in the hip joint through a hole 82 in the femur bone 7. The injecting member 92 comprises a piston 94 that pushes said fluid 93 into the mould 81.

Figure 47:
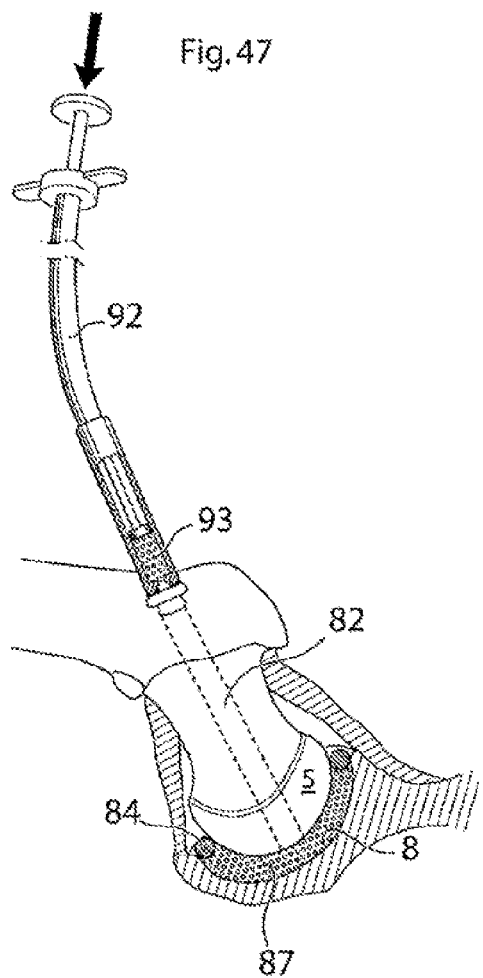
FIG. 47 shows the filling of a sealed area inside of the hip joint using an instrument that operates through the femur bone.

FIG. 47 shows the hip joint in section wherein an injecting member 92 injects a fluid 93 into a sealed area 87 in the hip joint through a hole 82 in the pelvic bone 9 from the opposite side from acetabulum 8. Said sealed area 87, being sealed by at least a first 84 sealing member. The injecting member 92 comprises a piston 94 that pushes said fluid 93 into the sealed area 87.

Figure 48:
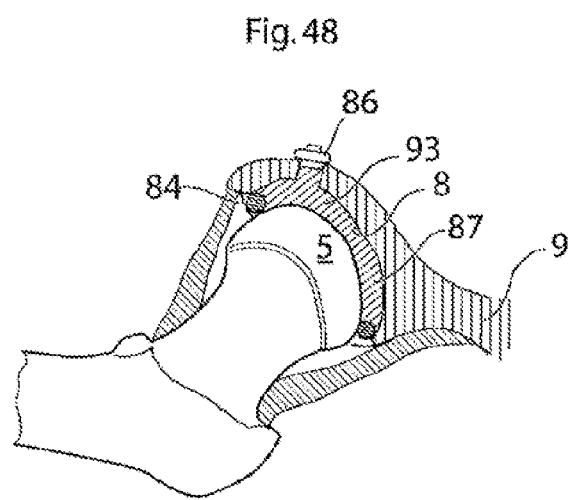
FIG. 48 shows a hip joint in section after a sealed area in the hip joint has been filled with a fluid.

FIG. 48 shows the sealed area 87, sealed by the first 84 and second 86 sealing member together with the caput femur 5 and the pelvic bone 9. A fluid adapted to harden 93 has been injected into said sealed area, and after the hardening of said fluid it provides at least one hip joint surface.

After the injecting member 92 has injected a fluid 93 into a mould 81 or a sealed are 87 it is being retracted from the area.

The mould 81 and the first and second sealing members 84,86 according to any of the embodiments can further be adapted to be resorbable by the human body or to melt after they have served their purpose.

After at least one hip joint surface has been provided through a hole 18 in the pelvic bone 9, in accordance with any of the embodiment above, said hole 18 needs to be closed.

Figure 49:
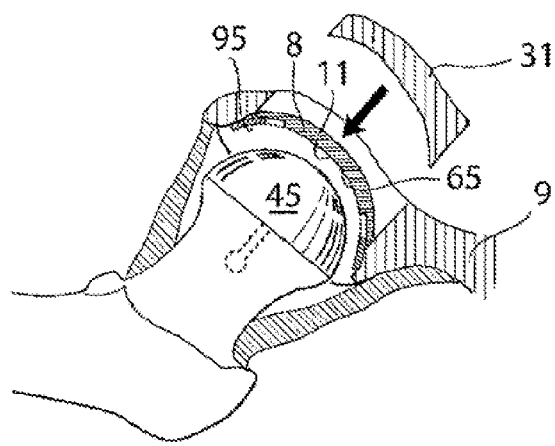
FIG. 49 shows the closing of a hole in the hip joint using a bone plug.

FIG. 49 shows the hip joint of a human patient in section wherein a bone plug 31 is placed in the hole 18 in the pelvic bone 9 to close said hole 18. According to a first embodiment the artificial acetabulum surface 65 comprises supporting members 94 which carries the load placed on the acetabulum 8 from weight of the human patient through the contact with the caput femur 5. Said supporting members can be adapted to be displaceable 97 supporting members. The bone plug 31 can be attached to the artificial acetabulum surface 11 and/or the pelvic bone 9 by means of bone cement, adhesive, screws, form fitting, welding, sprints, band or some other mechanical connecting member.

Figure 50:
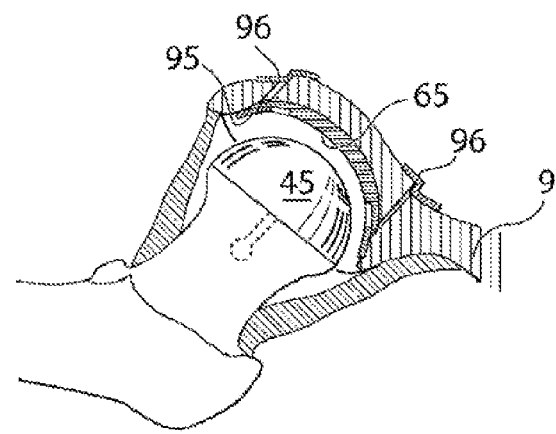
FIG. 50 shows the fixation of a bone plug in the pelvic bone.

FIG. 50 shows the hip joint of a human patient in section wherein the bone plug 31 placed in the hole 18 in the pelvic bone 9 is further supported by supporting means 96 placed between the bone plug 31 and the pelvic bone 9 on the opposite side from acetabulum 8 using at least one of: bone cement, adhesive, screws, form fitting, welding, sprints, band or some other mechanical connecting member.

Figure 51:
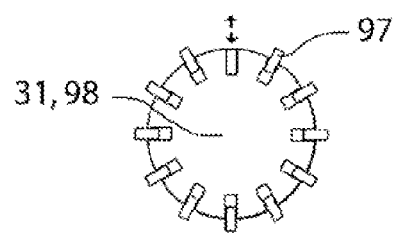
FIG. 51 shows a part for closing a hole in the pelvic bone having displaceable supporting members.

FIG. 51 shows a bone plug 31 or a prosthetic part 98 comprising several displaceable supporting members adapted to carry the load placed on the acetabulum 8 from weight of the human patient through the contact with the caput femur 5. The displaceable parts 97 are displaced into a corresponding part in or at the edge of the hole 18 in the pelvic bone 9.

Figure 52:
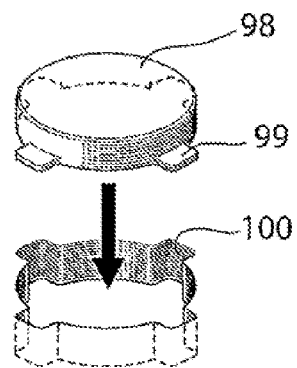
FIG. 52a shows a prosthetic part being used to close a hole in the pelvic bone.
FIG. 52b shows how sections of a prosthetic part is used as support against the edges of the hole in the pelvic bone.
FIG. 52c shows the insertion of a prosthetic part in the hole in the pelvic bone.
Figure 52:
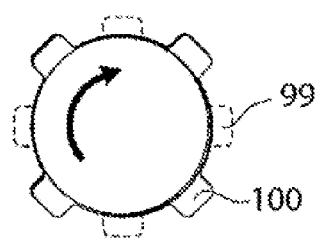
Figure 52:
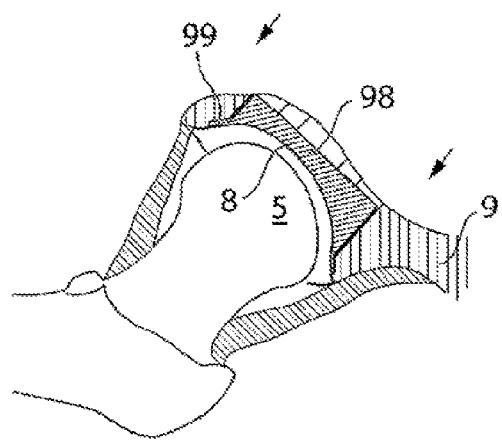

According to a second embodiment the closing of the hole 18 in the pelvic bone is done by means of a prosthetic part 98. FIG. 52a shows the prosthetic part 98 being inserted into a hole 18 in the pelvic bone 9 from the opposite side from acetabulum 8. According to one embodiment the prosthetic part 98 comprises supporting members 99 adapted to correspond with sections 100 of the hole 18 in the pelvic bone 9. After the prosthetic part 98 has been inserted into said hole 18 in the pelvic bone 9 it is rotated so that the supporting members 99 comes in contact with the pelvic bone 9 and can carry the load placed on the acetabulum 8 from weight of the human patient through the contact with the caput femur 5. Said prosthetic part 98 could also be adapted to serve as artificial acetabulum surface 65 according to any of the above mentioned embodiments.

FIG. 52b shows the prosthetic part 98 when rotated to carry the load placed on the acetabulum 8 from weight of the human patient through the contact with the caput femur 5.

FIG. 52c shows the hip joint of a human patient in section wherein the prosthetic part 98 closes the hole 18 in the pelvic bone 9 and carries the load placed on the acetabulum 8 from weight of the human patient through the contact with the caput femur 5 by means of the supporting members 99. The prosthetic part 98 can further be fixated to the pelvic bone 9 by means of bone cement, adhesive, screws, form fitting, welding, sprints, band or some other mechanical connecting member.

Figure 53:
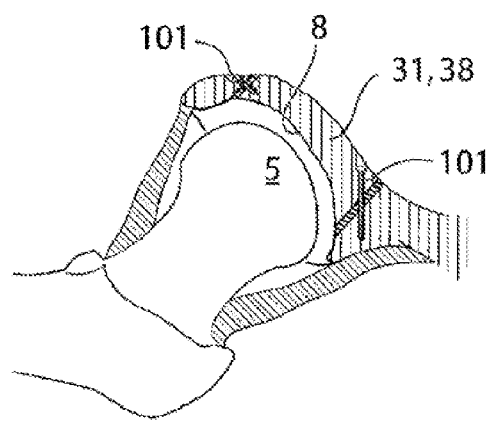
FIG. 53a shows how screws are being used to fixate a bone plug or a prosthetic part in the hole in the pelvic bone of a human patient.
FIG. 53b shows how a supporting plate is being used to fixate a bone plug or a prosthetic part in the hole in the pelvic bone of a human patient.
FIG. 53c shows two bone plugs or prosthetic parts being fixated using a supporting plate.
FIG. 53d shows a section of the hip joint after two holes in the pelvic bone have been filled with a fluid.

FIG. 53a shows the hip joint of a human patient in section wherein bone plug 31 or prosthetic part 98 is attached to the pelvic bone 9 by means of screws 101 placed from the opposite side from acetabulum 8. The screws 101 are possible to place in different angles depending on reach or need for support.

FIG. 53b shows the hip joint of a human patient in section wherein bone plug 31 or prosthetic part 98 is attached to the pelvic bone 9 by means of a plate 102 at least partly covering said bone plug 31 or prosthetic part 98. According to a first embodiment the plate 102 is attached to the pelvic bone 9 by means of screws 103 placed from the opposite side from acetabulum 8. However it is also conceivable that said screws 103 can be replaced or assisted by bone cement, adhesive, form fitting, welding, sprints, band or some other mechanical connecting member.

FIG. 53c shows the hip joint of a human patient in section wherein two bone plugs 31 or prosthetic parts 98 are attached to the pelvic bone 9 by means of a plate 102 at least partly covering said bone plugs 31 or prosthetic parts 98. According to a first embodiment the plate 102 is attached to the pelvic bone 9 by means of screws 103 placed from the opposite side from acetabulum 8. However it is also conceivable that said screws 103 can be replaced or assisted by bone cement, adhesive, form fitting, welding, sprints, band or some other mechanical connecting member. FIG. 53c also shows the provided artificial acetabulum surface 65.

FIG. 53d shows the hip joint of a human patient in section wherein two holes 18 in the pelvic bone has been covered by means of a fluid injected into said holes 18, through sealing members 104, said fluid 93 being adapted to harden. Further more a plate 102 has been provided at least partly covering said holes 18. According to a first embodiment the plate 102 is attached to the pelvic bone 9 by means of screws 103 placed from the opposite side from acetabulum 8. However it is also conceivable that said screws 103 can be replaced or assisted by bone cement, adhesive, form fitting, welding, sprints, band or some other mechanical connecting member. FIG. 53d also shows the provided artificial acetabulum surface 65, and the provided artificial caput femur surface 45.

Figure 54:
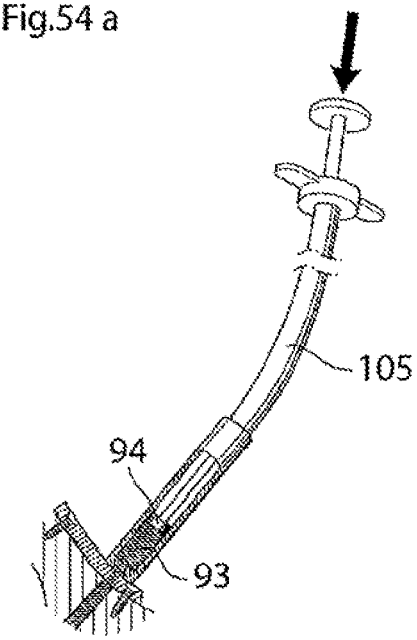
FIG. 54a shows an injecting member adapted to inject a fluid into an area of the hip joint.
FIG. 54b shows an injecting member adapted to inject a fluid into an area of the hip joint when injecting a fluid.
Figure 54:
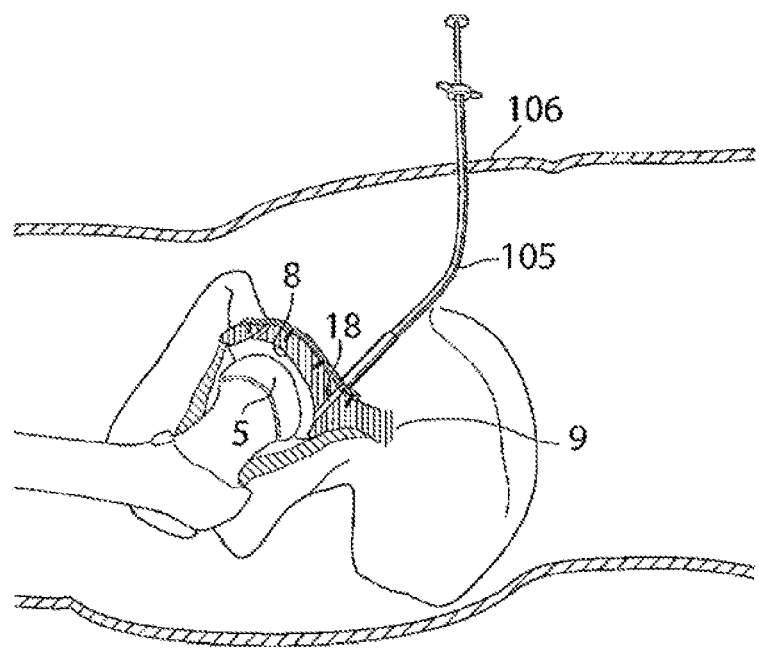

FIG. 54a shows an injecting member 105 for injecting a fluid adapted to harden 93, preferably bone cement or adhesive to be used as support in the closing of the hole 18 in the pelvic bone 9. The injecting member 105 comprises a piston 94 that pushes said fluid 93 the area where it is wanted.

FIG. 54b shows the injecting member 105 as it is inserted through the skin 106 of a human patient in the surgical or laparoscopic/arthroscopic method, and is further placed in connection with the hip joint through the hole 18 in the pelvic bone 9. The injecting member 105 is adapted to inject a fluid 93 adapted to harden.

Figure 55:
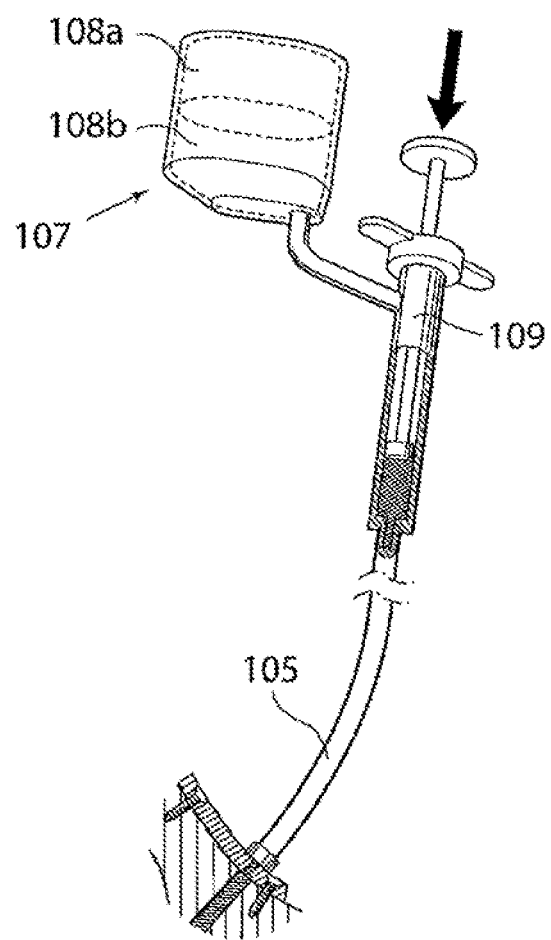
FIG. 55 shows an injecting member in further detail.

FIG. 55 shows the injecting member 105 according to any of the embodiments above, adapted to inject fluid 93 into a mould 81, a sealed area 87 or a connecting area between the pelvic bone 9 and a prosthetic part, the pelvic bone 9 and a bone plug 31 or the caput femur 5 and a prosthetic part. Said injecting member comprises a container 107 adapted to hold a fluid for injection. According to a first embodiment said container comprises two compartments 108a,b adapted to hold two different fluids, said fluids being adapted to harden when mixed. In the embodiment when the container 107 is adapted to hold two fluids, it is conceivable that the injecting member 105 further comprises a mixing member 109 wherein said two fluids are being mixed before injection. According to a second embodiment (not shown) said container 107 is adapted to keep said fluid sterile. According to a third embodiment (not shown) said container 107 is adapted to keep said fluid cold and according to a fourth embodiment (not shown) said container 107 is adapted to keep said fluid in a dark environment. Furthermore a combination of the above mentioned embodiments is conceivable.

After the step of closing the hole in the pelvic bone of the human patient is concluded all instruments are retracted and the final step of the surgical or laparoscopic/arthroscopic method is performed. The final step comprises suturing or stapling the affected tissue and finally suturing or stapling the skin of the human patient.

Figure 56:
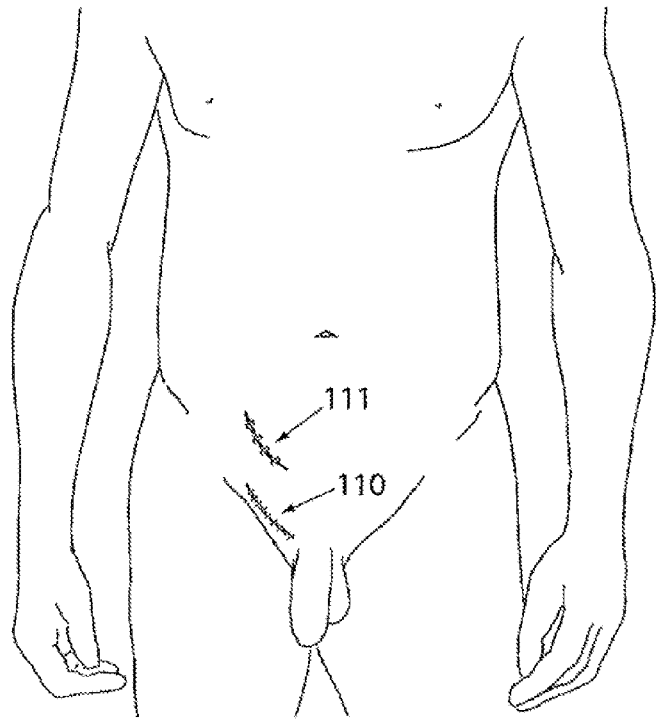
FIG. 56a shows the step of suturing or stapling in the surgical method.
FIG. 56b shows the step of suturing or stapling in the laparoscopic/arthroscopic method.
Figure 56:
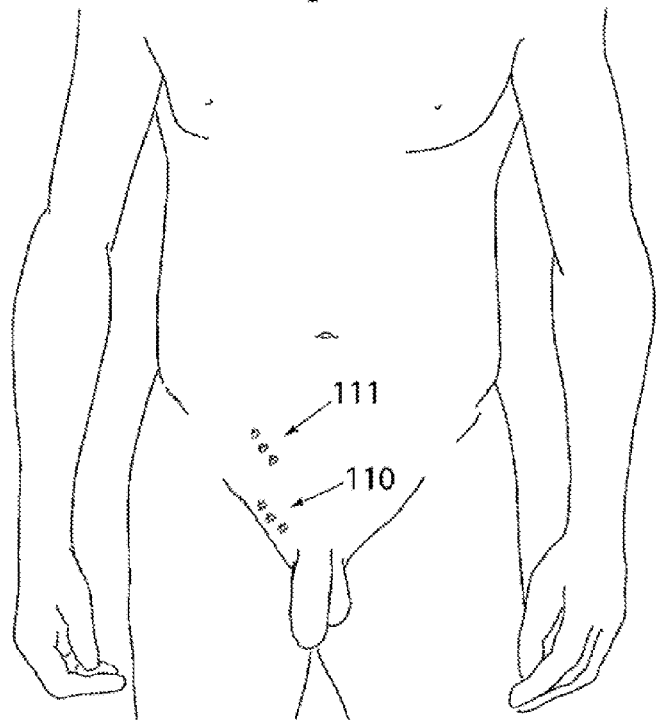

FIG. 56a shows the step of suturing 110 or stapling 111 the skin 106 of the human patient in the surgical method, whereas FIG. 56b shows the step of suturing 110 or stapling 111 the skin 106 of the human patient in the laparoscopic/arthroscopic method.

Please note that any embodiment or part of embodiment as well as any method or part of method could be combined in any way. All examples herein should be seen as part of the general description and therefore possible to combine in any way in general terms.

The invention claimed is:

1. A method of treating a hip joint of a human patient by providing at least one hip joint surface, said hip joint comprising a caput femur and an acetabulum, said method comprising the steps of:
   a) cutting the skin of the human patient,
   b) dissecting an area of the pelvic bone on the opposite side from the acetabulum,
   c) creating a hole in said dissected area from the opposite side from the acetabulum,
   said hole passing through the pelvic bone and into the hip joint of the human patient, and
   d) providing at least one hip joint surface to the hip joint from the opposite side from the acetabulum, through said hole in the pelvic bone of the human patient,
   wherein the step b) of dissecting an area of the pelvic bone comprises at least one of the following:
      dissecting an area between peritoneum and the pelvic bone,
      dissecting an area of the pelvic bone comprises dissecting an area between the pelvic bone and the surrounding tissue,
      dissecting an area of the pelvic bone comprises dissecting an area of the pelvic region, and
      dissecting an area of the pelvic bone comprises dissecting an area of the inguinal region,
   or, wherein the method in addition to the steps a)-d) above, further comprises at least one of the following additional steps:
      dissecting an area of the abdominal cavity,
      penetrating the hip joint capsule,
      removing or penetrating the tissue surrounding the pelvic bone in the area opposite to acetabulum.

2. The method according to claim 1, further comprising the step of using at least one camera and one or more surgical instruments for at least one of the following method steps:
   providing a rotating, oscillating, vibrating or repetitive movement,
   providing a rotating element and using rotating power from outside the body via the femoral bone,
   providing a rotating element and using rotating power from outside the body via the pelvic bone from the opposite side of the hip joint,
   providing a rotating element and using rotating power from the abdomen from the opposite side of the hip joint,
   dissecting to reach the hip joint,
   dissecting inside the hip joint via the femoral bone,
   dissecting inside the hip joint via the pelvic bone from the opposite side of the hip joint,
   dissecting inside the hip joint via the femoral capsule,
   reaming inside the hip joint via the femoral bone,
   reaming inside the hip joint via the pelvic bone from the opposite side of the hip joint,
   reaming inside the hip joint via the femoral capsule,
   moving parts or tissue to or from inside the hip joint via the femoral bone,
   moving parts or tissue to or from inside the hip joint via the pelvic bone from the opposite side of the hip joint,
   moving parts or tissue to or from inside the hip joint via the femoral capsule,
   creating and preparing new surfaces for placing the artificial hip joint surface inside the hip joint via the femoral bone,
   creating and preparing new surfaces for placing the artificial hip joint surface inside the hip joint via the pelvic bone from the opposite side of the hip joint,
   creating and preparing new surfaces for placing the artificial hip joint surface inside the hip joint via the femoral capsule,
   inserting at least one prosthetic part inside the hip joint via the femoral bone,
   inserting at least one prosthetic part inside the hip joint via the pelvic bone from the opposite side of the hip joint,
   inserting at least one prosthetic part inside the hip joint via the femoral capsule,
   placing at least one prosthetic part inside the hip joint via the femoral bone,
   placing at least one prosthetic part inside the hip joint via the pelvic bone from the opposite side of the hip joint,
   placing at least one prosthetic part inside the hip joint via the femoral capsule,
   connecting at least one prosthetic part inside the hip joint via the femoral bone,
   connecting at least one prosthetic part inside the hip joint via the pelvic bone from the opposite side of the hip joint,
   connecting at least two prosthetic parts to each other inside the hip joint via the femoral capsule,
   fixating with bone cement or mechanical elements in the hip joint at least one prosthetic part inside the hip joint via the femoral bone,
   fixating with bone cement or mechanical elements in the hip joint at least one prosthetic part inside the hip joint via the pelvic bone from the opposite side of the hip joint, fixating with bone cement or mechanical elements in the hip joint at least one prosthetic part inside the hip joint via the femoral capsule,
attaching at least two prosthetic parts to each other inside the hip joint via the femoral bone,
attaching at least two prosthetic parts to each other inside the hip joint via the pelvic bone from the opposite side of the hip joint,
attaching at least two prosthetic parts to each other inside the hip joint via the femoral capsule,
attaching in the hip joint at least one prosthetic part inside the hip joint via the femoral bone,
attaching in the hip joint at least one prosthetic part inside the hip joint via the pelvic bone from the opposite side of the hip joint,
attaching in the hip joint at least one prosthetic part inside the hip joint via the femoral capsule,
filling at least one prosthetic part inside the hip joint via the femoral bone,
filling at least one prosthetic part inside the hip joint via the pelvic bone from the opposite side of the hip joint, and
filling at least one prosthetic part inside the hip joint via the femoral capsule.

3. The method according to claim 1, wherein the method step of dissecting an area of the pelvic bone on the opposite side from the acetabulum comprises the step of removing or penetrating the tissue surrounding the pelvic bone in the area opposite to acetabulum which enables the surgeon to reach the pelvic bone.

4. The method according to claim 1, wherein the step of providing at least one hip joint surface to the hip joint from the opposite side from the acetabulum through said hole in the pelvic bone of the human patient further comprises at least one of the following parallel steps of:
entering the hip joint through the hip joint capsule, and
entering the hip joint through the femur bone.

5. The method of treating a hip joint of a human patient according to claim 1, further comprising the step of creating said hole in said dissected area using a surgical cutting instrument wherein said hole is a through-going hole in the acetabulum area from the abdominal side of the pelvic bone of said human patient, and wherein said instrument comprises:
a driving member,
a bone contacting member in connection with said driving member, wherein said bone contacting member is adapted to create said hole,
an operating device adapted to operate said driving member, said method further comprising the steps of:
operating said driving member, and
creating said hole in the acetabulum area starting from the abdominal side of the pelvic bone of the human patient through repetitive or continuous movement using said bone contacting member of said instrument.

6. The method according to claim 5, wherein said driving member and bone contacting member together from an elongated member, and further comprises the step of placing said elongated member to achieve a first supporting point for the bone contacting member in the femoral bone and a second supporting point in a pelvic bone.

7. The method according to claim 6, wherein said elongated member is adapted to receive said force from an operation device outside the body, lateral of the proximal femoral bone.

8. The method according to claim 6, wherein said elongated member is receiving said force from an operation device in the abdomen.

9. The method according to claim 6, further comprising the step of connecting an operation device giving force to said driving member from outside the body, lateral on the opposite side of said hip joint outside the opposite side ilium pelvic bone outside the body.

10. The method of treating a hip joint of a human patient according to claim 1, further comprising the step of fixating the hip joint surface to the caput femur, or next other portion of the femoral bone, or to the pelvic bone.

11. The method of treating a hip joint of a human patient according to claim 10, wherein said fixation is performed by means of mechanical fixating members, bone cement or adhesive.

12. The method of treating a hip joint of a human patient according to claim 1, and further comprising the step of closing said hole in the pelvic bone, wherein said closing of said hole in the pelvic bone is performed by means of bone cement, a bone plug, or a prosthetic part.

13. The method of treating a hip joint of a human patient according to claim 1, wherein the step of providing at least one hip joint surface to the hip joint from the opposite side from the acetabulum comprises providing at least one of: an artificial caput femur, an artificial caput femur surface, an artificial acetabulum and an artificial acetabulum surface, and wherein the method further comprises the step of: mounting said at least one hip joint surface in said hip joint.

14. The method of treating a hip joint of a human patient according to claim 13, wherein the step of providing an artificial acetabulum surface comprises providing an artificial acetabulum surface comprising at least one supporting member, wherein said supporting member comprises at least one of the following:
screws,
adhesive,
at least one plate,
bone cement,
a section of said artificial acetabulum, or
other mechanical supporting constructions.

15. The method of treating a hip joint of a human patient according to claim 14, wherein said supporting member comprises a first and second part, the method further comprises the step of displacing said second part in relation to said first part, wherein said second part is carrying said load by the connection with the pelvic bone and is carrying said load when displaced.

16. The method of treating a hip joint of a human patient according to claim 13, further comprising the step of inserting said at least two artificial caput femur surface parts into a hip joint using a surgical insertion instrument wherein said at least two artificial caput femur surface parts are inserted through at least one of:
the pelvic bone, and
the femur bone.

17. The method of treating a hip joint of a human patient according to claim 13, further comprising the step of inserting said at least two artificial acetabulum surface parts into a hip joint using a surgical insertion instrument wherein said at least two artificial acetabulum surface parts are inserted through at least one of:
the pelvic bone, or
the femur bone.

18. The method of treating a hip joint of a human patient according to claim 13, wherein the step of providing an artificial caput femur surface comprises providing an artificial caput femur surface comprising at least two caput femur surface parts connected to each other after insertion in a hip joint of a human patient to form an artificial caput femur surface.

19. The method of treating a hip joint of a human patient according to claim 18, wherein said at least two artificial caput femur surface parts are mechanically connecting using at least one of the following:
    at least one screw,
    at least one pin,
    at least one portion of at least one of the parts adapted to be introduced into the other part,
    the parts being adapted to be sliding into the other part,
    form fitting,
    welding,
    adhesive,
    pin,
    wire,
    a ball mounted into a bowl being portions of said parts,
    a male portion of one part mounted into a female portion of the other part,
    a key introduced into a lock being portions of said parts,
    band, and
    other mechanical connecting members.

20. The method of treating a hip joint of a human patient according to claim 18, wherein the step of providing an artificial caput femur surface comprises providing an artificial caput femur surface being hollow and having a greatest internal cross-sectional diameter and comprising an opening, said opening being adapted to have a diameter or cross sectional distance less than said greatest internal cross-sectional diameter of said hollow medical device when mounted on the caput femur of a human patient, wherein said hollow medical device further is adapted to:
    have a diameter of said opening of said hollow medical device larger than the diameter of the caput femur, when introduced onto the caput femur, and
    have at least the smallest distance of said opening diameter or cross sectional distance being smaller than said greatest internal cross-sectional diameter of said hollow medical device, after mounting said device on said caput femur and in a functional position thereon,
    thereby allowing the method steps of:
        mounting said artificial caput femur surface on said caput femur, which requires an opening diameter or cross sectional distance larger that the diameter of caput femur, and
        decreasing said opening to become smaller than said greatest internal cross-sectional area of said hollow medical device after mounting on the caput femur.

21. The method of treating a hip joint of a human patient according to claim 20, wherein said artificial caput femur surface further comprises at least one slit allowing the method steps of, mounting said artificial caput femur surface on said caput femur.

22. The method of treating a hip joint of a human patient according to claim 20, wherein said artificial caput femur surface is partially spherical.

23. The method of treating a hip joint of a human patient according to claim 13, wherein the step of creating a hole in the said dissected area comprises creating a hole having a diameter larger than the largest diameter of an artificial caput femur of the patient, thus allowing an artificial caput femur to pass through said hole.

24. The method of treating a hip joint of a human patient according to claim 13, wherein the step of providing an artificial acetabulum surface comprises providing an artificial acetabulum surface comprising at least two acetabulum surface parts, and wherein said at least two artificial acetabulum surface parts are further connected to each other after insertion in a hip joint of a human patient and forming an artificial acetabulum surface.

25. The method of treating a hip joint of a human patient according to claim 24, wherein said at least two artificial acetabulum surface parts are mechanically connecting using at least one of the following:
    at least one screw,
    at least one pin,
    at least one portion of at least one of the parts adapted to be introduced into the other part,
    the parts being adapted to be sliding into the other part,
    form fitting,
    welding,
    adhesive,
    pin,
    wire,
    a ball mounted into a bowl being portions of said parts,
    a male portion of one part mounted into a female portion of the other part,
    a key introduced into a lock being portions of said parts,
    band, and
    other mechanical connecting members.

26. A method of treating a hip joint of a human patient by providing at least one hip joint surface, said hip joint comprising a caput femur and an acetabulum, said method comprising the steps of:
    inserting a needle or a tubular instrument into the patient's body,
    using the needle or tubular instrument to fill a part of the patient's body with gas and thereby expanding a cavity within the body, wherein said cavity is located in a region such that the opposite side of the pelvic bone is reachable,
    placing at least two laparoscopic/arthroscopic trocars in said cavity,
    inserting a camera through one of the laparoscopic/arthroscopic trocars into said cavity,
    inserting at least one dissecting tool through one of said at least two laparoscopic/arthroscopic trocars,
    dissecting an area of the pelvic bone on the opposite side from the acetabulum,
    creating a hole in said dissected area from the opposite side from the acetabulum,
    said hole passing through the pelvic bone and into the hip joint of the human patient, and
    providing at least one hip joint surface to the hip joint from the opposite side from the acetabulum, through said hole in the pelvic bone of the human patient, and
    closing said hole in the pelvic bone, wherein said closing of said hole in the pelvic bone is performed by means of bone cement, a bone plug, or a prosthetic part.

27. The method of treating a hip joint of a human patient according to claim 26, wherein the step of providing at least one hip joint surface to the hip joint from the opposite side from the acetabulum comprises providing at least one of: an artificial caput femur, an artificial caput femur surface, an artificial acetabulum and an artificial acetabulum surface, wherein the method further comprising the step of, mounting said at least one hip joint surface in said hip joint.

28. The method of treating a hip joint of a human patient according to claim 27, wherein the step of providing an artificial acetabulum surface comprises providing an artificial acetabulum surface comprising at least one supporting member, wherein said at least one supporting member comprises at least one of the following:
  screws,
  adhesive,
  at least one plate,
  bone cement,
  a section of said artificial acetabulum, or
  other mechanical supporting constructions.

29. The method of treating a hip joint of a human patient according to claim 28, wherein said supporting member comprises a first and second part, and the method further comprises the steps of:
  displacing said second part in relation to said first part, wherein said second part is carrying said load by the connection with the pelvic bone, and
  is carrying said load when displaced.

30. The method of treating a hip joint of a human patient according to claim 27, wherein the step of providing an artificial acetabulum surface comprises providing an artificial acetabulum surface comprising at least two acetabulum surface parts, and wherein said at least two artificial acetabulum surface parts are further connected to each other after insertion in a hip joint of a human patient and forming an artificial acetabulum surface.

31. The method of treating a hip joint of a human patient according to claim 30, wherein said at least two artificial acetabulum surface parts are mechanically connected using at least one of the following:
  at least one screw,
  at least one pin,
  at least one portion of at least one of the parts adapted to be introduced into the other part,
  the parts being adapted to be sliding into the other part,
  form fitting,
  welding,
  adhesive,
  pin,
  wire,
  a ball mounted into a bowl being portions of said parts,
  a male portion of one part mounted into a female portion of the other part,
  a key introduced into a lock being portions of said parts,
  band, and
  other mechanical connecting members.

32. The method of treating a hip joint of a human patient according to claim 27, wherein the step of creating a hole in said dissected area comprises creating a hole having a diameter larger than the largest diameter of an artificial caput femur of the patient, thus allowing an artificial caput femur to pass through said hole.

33. The method of treating a hip joint of a human patient according to claim 27, wherein the step of providing an artificial caput femur surface comprises providing an artificial caput femur surface comprising at least two caput femur surface parts connected to each other after insertion in a hip joint of a human patient to form an artificial caput femur surface.

34. The method of treating a hip joint of a human patient according to claim 33, wherein said at least two artificial caput femur surface parts are mechanically connected using at least one of the following:
  at least one screw,
  at least one pin,
  at least one portion of at least one of the parts adapted to be introduced into the other part,
  the parts being adapted to be sliding into the other part,
  form fitting,
  welding,
  adhesive,
  pin,
  wire,
  a ball mounted into a bowl being portions of said parts,
  a male portion of one part mounted into a female portion of the other part,
  a key introduced into a lock being portions of said parts,
  band, and
  other mechanical connecting members.

35. The method of treating a hip joint of a human patient according to claim 33, wherein the step of providing an artificial caput femur surface comprises the step of providing an artificial caput femur surface being hollow and having a greatest internal cross-sectional diameter and comprising an opening, said opening being adapted to have a diameter or cross sectional distance less than said greatest internal cross-sectional diameter of said hollow medical device when mounted on the caput femur of a human patient, wherein said hollow medical device is adapted to:
  have a diameter of said opening of said hollow medical device larger than the diameter of the caput femur, when introduced onto the caput femur, and
  have at least the smallest distance of said opening diameter or cross sectional distance being smaller than said greatest internal cross-sectional diameter of said hollow medical device, after mounting said device on said caput femur and in a functional position thereon,
thereby allowing the method steps of:
  mounting said artificial caput femur surface on said caput femur, which requires an opening diameter or cross sectional distance larger that the diameter of caput femur, and
  decreasing said opening to become smaller than said greatest internal cross-sectional area of said hollow medical device after mounting on the caput femur.

36. The method of treating a hip joint of a human patient according to claim 35, wherein said artificial caput femur surface further comprises at least one slit allowing the method steps of, mounting said artificial caput femur surface on said caput femur.

37. The method of treating a hip joint of a human patient according to claim 35, wherein said artificial caput femur surface is partially spherical.

38. The method of treating a hip joint of a human patient according to claim 27, further comprising the step of inserting said at least two artificial acetabulum surface parts into a hip joint using a surgical insertion instrument, said at least two artificial acetabulum surface parts are inserted through at least one of:
  the pelvic bone, or
  the femur bone.

39. The method of treating a hip joint of a human patient according to claim 27, further comprising the step of inserting said at least two artificial caput femur surface parts into a hip joint using a surgical insertion instrument, wherein said at least two artificial caput femur surface parts are inserted through at least one of:
  the pelvic bone, and
  the femur bone.

40. The method of treating a hip joint of a human patient according to claim 26, further comprising the step of reaming the acetabulum.

41. The method of treating a hip joint of a human patient according to claim 26, further comprising the step of reaming the caput femur.

42. The method of treating a hip joint of a human patient according to claim 26 further comprising the step of placing a mold inside of the hip joint of the human patient and injecting a fluid into said mold placed inside of the hip joint of the human patient.

43. The method of treating a hip joint of a human patient according to claim 26, further comprising the steps of:
placing at least one sealing member between the acetabulum and the caput femur, thus creating a sealed area between the acetabulum and the caput femur, and
injecting a fluid into said sealed area,
wherein said fluid changing from fluid to solid form.

44. The method of treating a hip joint of a human patient according to claim 26, further comprising the step of withdrawing instruments.

45. The method of treating a hip joint of a human patient according to claim 26, further comprising the step of closing the skin of the human patient using sutures or staples.

46. The method of treating a hip joint of a human patient according to claim 26, wherein the step of cutting the skin of the human patient is performed in the abdominal wall of the human patient.

47. The method of treating a hip joint of a human patient according to claim 26, wherein the step of cutting the skin of the human patient is performed in the inguinal area of the human patient.

48. The method of treating a hip joint of a human patient according to claim 26, wherein the step of cutting the skin of the human patient is performed in the pelvic region of the human patient.

49. The method of treating a hip joint of a human patient according to claim 26, wherein the step of dissecting an area of the pelvic bone comprises dissecting an area of the abdominal cavity.

50. The method of treating a hip joint of a human patient according to claim 26, wherein the step of dissecting an area of the pelvic bone comprises dissecting an area between peritoneum and the pelvic bone.

51. The method of treating a hip joint of a human patient according to claim 26, wherein the step of dissecting an area of the pelvic bone comprises dissecting an area between the pelvic bone and the surrounding tissue.

52. The method of treating a hip joint of a human patient according to claim 26, wherein the step of dissecting an area of the pelvic bone comprises dissecting an area of the pelvic region.

53. The method of treating a hip joint of a human patient according to claim 26, wherein the step of dissecting an area of the pelvic bone comprises dissecting an area of the inguinal region.

54. The method of treating a hip joint of a human patient according to claim 26, further comprising the step of creating said hole in said dissected area using a surgical cutting instrument, wherein said hole is a through-going hole in the acetabulum area from the abdominal side of the pelvic bone of said human patient, and wherein said instrument comprises:
a driving member,
a bone contacting member in connection with said driving member, wherein said bone contacting member is adapted to create said hole,
an operating device adapted to operate said driving member, said method further comprising the steps of:
operating said driving member, and
creating said hole in the acetabulum area starting from the abdominal side of the pelvic bone of the human patient through repetitive or continuous movement using said bone contacting member of said instrument.

55. The method according to any of claim 54, wherein said driving member and bone contacting member together form an elongated member, the method further comprising placing said elongated member to achieve a first supporting point for the bone contacting member in the femoral bone and a second supporting point in a pelvic bone.

56. The method according to claim 54, wherein said elongated member is adapted to receive said force from an operation device outside the body, lateral of the proximal femoral bone.

57. The method according to claim 54, wherein said elongated member is receiving said force from an operation device in the abdomen.

58. The method according to claim 54, further comprising the step of connecting an operation device giving force to said driving member from outside the body, lateral on the opposite side of said hip joint outside the opposite side ilium pelvic bone outside the body.

59. The method according to claim 26, wherein the method includes the step of providing at least one hip joint surface to the hip joint from the opposite side from the acetabulum through said hole in the pelvic bone of the human patient, and wherein the method further comprises at least one of the following parallel steps of:
entering the hip joint through the hip joint capsule, and
entering the hip joint through the femur bone.

60. The method according to claim 26, wherein the method
step of dissecting an area of the pelvic bone on the opposite side from the acetabulum comprises the step of dissecting two or more of the following areas:
an area in the abdominal cavity,
an area between peritoneum and the pelvic bone,
an area of the pelvic bone and surrounding tissue,
the pelvic region, and
an area of the pelvic bone that comprises the inguinal area,
in all cases in order to dissect the pelvic bone on the opposite side of the acetabulum.

61. The method according to claim 26, wherein the method
step of dissecting an area of the pelvic bone on the opposite side from the acetabulum comprises the step of removing or penetrating the tissue surrounding the pelvic bone in the area opposite to acetabulum which enables the surgeon to reach the pelvic bone.

62. The method according to claim 26, further comprises the step of using at least one camera and one or more surgical instruments for at least one of the following method steps:
providing a rotating, oscillating, vibrating or repetitive movement,
providing a rotating element and using rotating power from outside the body via the femoral bone,
providing a rotating element and using rotating power from outside the body via the pelvic bone from the opposite side of the hip joint,
providing a rotating element and using rotating power from the abdomen from the opposite side of the hip joint,
dissecting to reach the hip joint,
dissecting inside the hip joint via the femoral bone,
dissecting inside the hip joint via the pelvic bone from the opposite side of the hip joint,
dissecting inside the hip joint via the femoral capsule, reaming inside the hip joint via the femoral bone,
reaming inside the hip joint via the pelvic bone from the opposite side of the hip joint,
reaming inside the hip joint via the femoral capsule,
moving parts or tissue to or from inside the hip joint via the femoral bone,
moving parts or tissue to or from inside the hip joint via the pelvic bone from the opposite side of the hip joint,
moving parts or tissue to or from inside the hip joint via the femoral capsule,
creating and preparing new surfaces for placing the artificial hip joint surface inside the hip joint via the femoral bone,
creating and preparing new surfaces for placing the artificial hip joint surface inside the hip joint via the pelvic bone from the opposite side of the hip joint,
creating and preparing new surfaces for placing the artificial hip joint surface inside the hip joint via the femoral capsule,
inserting at least one prosthetic part inside the hip joint via the femoral bone,
inserting at least one prosthetic part inside the hip joint via the pelvic bone from the opposite side of the hip joint,
inserting at least one prosthetic part inside the hip joint via the femoral capsule,
placing at least one prosthetic part inside the hip joint via the femoral bone,
placing at least one prosthetic part inside the hip joint via the pelvic bone from the opposite side of the hip joint,
placing at least one prosthetic part inside the hip joint via the femoral capsule,
connecting at least one prosthetic part inside the hip joint via the femoral bone,
connecting at least one prosthetic part inside the hip joint via the pelvic bone from the opposite side of the hip joint,
connecting at least one prosthetic part inside the hip joint via the femoral capsule,
fixating with bone cement or mechanical elements in the hip joint at least one prosthetic part inside the hip joint via the femoral bone,
fixating with bone cement or mechanical elements in the hip joint at least one prosthetic part inside the hip joint via the pelvic bone from the opposite side of the hip joint,
fixating with bone cement or mechanical elements in the hip joint at least one prosthetic part inside the hip joint via the femoral capsule,
attaching at least two prosthetic parts to each other inside the hip joint via the femoral bone,
attaching at least two prosthetic parts to each other inside the hip joint via the pelvic bone from the opposite side of the hip joint,
attaching at least two prosthetic parts to each other inside the hip joint via the femoral capsule,
attaching in the hip joint at least one prosthetic part inside the hip joint via the femoral bone,
attaching in the hip joint at least one prosthetic part inside the hip joint via the pelvic bone from the opposite side of the hip joint,
attaching in the hip joint at least one prosthetic part inside the hip joint via the femoral capsule,
filling at least one prosthetic part inside the hip joint via the femoral bone,
filling at least one prosthetic part inside the hip joint via the pelvic bone from the opposite side of the hip joint, and
filling at least one prosthetic part inside the hip joint via the femoral capsule.

\* \* \* \* \*